(12) United States Patent
Blanckenberg et al.

(10) Patent No.: US 11,814,402 B2
(45) Date of Patent: Nov. 14, 2023

(54) BINUCLEAR PALLADACYCLES AND THEIR USE IN THE TREATMENT OF CANCER

(71) Applicants: Stellenbosch University, Stellenbosch (ZA); University of Cape Town, Cape Town (ZA)

(72) Inventors: Angelique Blanckenberg, Somerset West (ZA); Annick Van Niekerk, Strand (ZA); Selwyn Frank Mapolie, Kensington (ZA); Sharon Prince, Garlandale (ZA)

(73) Assignees: Stellenbosch University, Stellenbosch (ZA); University of Cape Town, Cape Town (ZA)

( * ) Notice: Subject to any disclaimer, the term of this patent is extended or adjusted under 35 U.S.C. 154(b) by 188 days.

(21) Appl. No.: 16/960,967

(22) PCT Filed: Feb. 15, 2019

(86) PCT No.: PCT/IB2019/051223
§ 371 (c)(1),
(2) Date: Jul. 9, 2020

(87) PCT Pub. No.: WO2019/159114
PCT Pub. Date: Aug. 22, 2019

(65) Prior Publication Data
US 2020/0339616 A1    Oct. 29, 2020

(51) Int. Cl.
*C07F 15/00* (2006.01)
*A61P 35/00* (2006.01)
*A61K 31/66* (2006.01)

(52) U.S. Cl.
CPC ............ *C07F 15/006* (2013.01); *A61K 31/66* (2013.01); *A61P 35/00* (2018.01)

(58) Field of Classification Search
CPC ..................................................... C07F 15/006
See application file for complete search history.

(56) References Cited

PUBLICATIONS

Apr. 12, 2019—International Search Report & Written Opinion for PCT/IB2019/051223.
Aliwaini et al., "A novel binuclear palladacycle complex inhibits melanoma growth in vitro and in vivo through apoptosis and autophagy," Biochemical Pharmacology, vol. 86, No. 12, pp. 1650-1663 (Oct. 4, 2013).
Zhao et al., "Self-assembly of indolocarbazole-containing macrocyclic molecules," Organic & Biomolecular Chemistry, vol. 8, pp. 3923-3927 (2010).
Li et al., "Synthesis and characterization of 5-substituted 8-hydroxyquinoline derivatives and their metal complexes," Tetrahedron, vol. 64, pp. 10986-10995 (2008).

(Continued)

*Primary Examiner* — Benjamin J Packard
(74) *Attorney, Agent, or Firm* — Banner & Witcoff, Ltd.

(57) ABSTRACT

This invention relates to a series of binuclear palladacycle compounds, and methods for the production of these compounds, that are suitable for use in the treatment of cancer. In particular embodiments, $R^1$ is phenyl substituted with two occurrences of isopropyl, $R^2$ is Cl, and $R^3$ is independently one or more substituents selected from —O(CH$_2$)$_2$O(CH$_2$)$_2$OH, —O(CH$_2$)$_2$O(CH$_2$)$_2$O(CH$_2$)$_2$OH, —O(CH$_2$)$_2$OH, and —O(CH$_2$)$_2$O(CH$_2$)$_2$OCH$_3$.

17 Claims, 4 Drawing Sheets

(56) References Cited

PUBLICATIONS

Aronov et al., "Folate-Targeted PEG as a Potential Carrier for Carboplatin Analogs. Synthesis and in Vitro Studies," Bioconjugate Chem., vol. 14, No. 3, pp. 563-574 (2003).

Ertl et al., "Sweetness and light: Sugar-functionalized CN and NN ligands in [Ir(CN)2(NN)]Cl complexes," Journal of Organometallic Chemistry, vol. 849-850, pp. 54-62 (2017).

Mungwe et al., "Cationic palladacycles as catalyst precursors for phenyl acetylene polymerization," Journal of Organometallic Chemistry, vol. 696, pp. 3527-3535 (2011).

Table 4.5: 1H NMR data for substituted binuclear palladacycles, BTC1-BTC4.

| Complex | CH=N | Aromatic Region | P-(CH₂)ₙ-P | (OCH₂CH₂)₂OH | (CH₃)₂CH | CH(CH₃)₂ |
|---|---|---|---|---|---|---|
| BTC1 | 7.89 (d, 2H, ⁴J_HP = 7.9 Hz) | 8.14-8.20 (m, 8H); 7.15-7.31 (m, 20H); 6.47 (dd, 2H, ³J_HH = 8.2 Hz and ⁴J_HH = 2.2 Hz); 5.62-5.65 (m, 2H) | 5.04-5.13 (m, 2H) | 3.66-3.67 (m, 4H, Ph-OCH₂-); 3.39-3.52 (m, 8H, Ph-OCH₂CH₂CH₂- and -CH₂CH₂OH); 3.15-3.19 (m, 4H, -CH₂-CH₂OH) | 3.39-3.52 (m, 4H) | 1.42 (d, 12H, ³J_HH = 6.9 Hz); 1.24 (d, 12H, ³J_HH = 6.9 Hz) |
| BTC2 | 7.88-7.89 (m, 2H) | 7.84-7.87 (m, 8H); 7.25-7.31 (m, 4H); 7.23-7.26 (m, 13H); 7.17 (d, 4H, ³J_HH = 8.2 Hz and ⁴J_HH = 7.6 Hz); 5.85-5.86 (m, 2H) | 3.63 (d, 4H, ³J_HH = 2.3 Hz) | 3.60-3.61 (m, 4H, Ph-OCH₂-); 3.34-3.42 (m, 8H, Ph-OCH₂CH₂OH); 3.11 (t, 4H, ³J_HH = 4.7 Hz, -CH₂-CH₂OH) | 3.34-3.42 (m, 4H) | 1.32 (d, 12H, ³J_HH = 7.0 Hz); 1.17 (d, 12H, ³J_HH = 7.0 Hz) |
| BTC3 | 7.91 (d, 2H, ⁴J_HP = 7.6 Hz) | 7.77-7.80 (m, 8H); 7.33 (m, 2H); 7.25-7.26 (m, 4H); 7.19 (d, 4H, ³J_HH = 7.8 Hz); 6.52 (dd, 2H, ³J_HH = 8.2 Hz and ⁴J_HH = 2.3 Hz); 5.86-5.89 (m, 2H) | 2.59-2.64 (m, 4H); 1.80 (m, 2H) | 3.66-3.68 (m, 4H, Ph-OCH₂-); 3.47-3.46 (m, 8H, Ph-OCH₂CH₂OH); 3.43-3.45 (m, 4H, -CH₂CH₂OH); 3.26-3.22 (m, 4H, -CH₂CH₂OH) | 3.34-3.38 (m, 4H) | 1.30 (d, 12H, ³J_HH = 6.5 Hz); 1.18 (d, 12H, ³J_HH = 7.0 Hz) |
| BTC4 | 7.95 (d, 2H, ⁴J_HP = 8.6 Hz) | 7.59-7.63 (m, 8H); 7.35-7.38 (m, 4H); 7.33 (m, 2H); 7.24-7.27 (m, 6H); 7.22 (d, 2H, ³J_HH = 7.8 Hz); 7.18 (d, 4H, ³J_HH = 7.3 Hz); 6.60 (dd, 2H, ³J_HH = 8.2 Hz and ⁴J_HH = 2.3 Hz); 5.83 (dd, 2H, ³J_HH = 5.7 Hz and ⁴J_HH = 2.3 Hz) | 5.09 (p, 3H, 4H, CF ring); 4.42-4.43 (m, 4H, CF ring) | 3.68-3.73 (m, 4H, Ph-OCH₂-); 3.52-3.54 (m, 8H, Ph-OCH₂CH₂OH); 3.23 (br t, 4H, -CH₂CH₂OH) | 3.39-3.43 (m, 4H) | 1.34 (d, 12H, ³J_HH = 7.0 Hz); 1.16 (d, 12H, ³J_HH = 7.0 Hz) |

Spectra run in CDCl₃ at 25 °C. Chemical shifts reported in ppm, referenced relative to residual solvent peak.

Figure 2

BC1: R = dppm and $R^3$ = H
BC2/AJ5: R = dppe and $R^3$ = H
BC3: R = dppp and $R^3$ = H
BC4: R = dppf and $R^3$ = H
BTC1: R = dppm and $R^3$ = (OCH$_2$CH$_2$)$_2$OH
BTC2: R = dppe and $R^3$ = (OCH$_2$CH$_2$)$_2$OH
BTC3: R = dppp and $R^3$ = (OCH$_2$CH$_2$)$_2$OH
BTC4: R = dppf and $R^3$ = (OCH$_2$CH$_2$)$_2$OH
BTC5: R = dppe and $R^3$ = (OCH$_2$CH$_2$)OH
BTC6: R = dppe and $R^3$ = (OCH$_2$CH$_2$)$_3$OH

| W Blot | UT | BTC2 | |
|---|---|---|---|
| Time (hrs) | 0 | 24 | 48 |
| γ-H2AX | | | |
| P38 | | | |

| W Blot | UT | BTC2 |
|---|---|---|
| Time (hrs) | 0 | 24 |
| Total PARP 116 KD | | |
| Cleaved PARP 86 KD | | |
| P38 | | |

Figure 5

BINUCLEAR PALLADACYCLES AND THEIR USE IN THE TREATMENT OF CANCER

CROSS-REFERENCE TO RELATED APPLICATIONS

This application is a U.S. National Stage application under 35 U.S.C. § 371 of International Application PCT/IB2019/051223, filed Feb. 15, 2019, which claims the benefit of priority to International Application PCT/IB2018/050957, filed Feb. 16, 2018. Benefit of the filing date of each of these prior applications is hereby claimed. Each of these prior applications is hereby incorporated by reference in its entirety.

INTRODUCTION

This invention relates to novel binuclear palladacycle compounds and methods for the production of these compounds. The invention further provides for pharmaceutical compositions comprising these compounds, and the use of these compounds and compositions in the treatment of diseases or disorders, in particular but not exclusively, in the treatment of cancer.

BACKGROUND

Since the discovery of cisplatin, in 1969, many different transition metals-based compounds have been tested as drugs/pharmaceutical agents (anti-cancer, anti-microbial and anti-fungal), including vanadium, iron, copper, ruthenium, palladium, silver and gold complexes.

Metallocycles of the platinum group metals, including palladacycles, have been found to be active as anti-cancer agents in vitro. Palladacycles are organometallic compounds with metal-carbon sigma bonds. They tend to form rings which are stabilized, intramolecularly, by two-electron donors, such as nitrogen.

The most significant advantage of palladium complexes is that they are less toxic than platinum complexes. However, one of the concerns with employing palladium compounds over platinum compounds is the enhanced lability of the ligands due to the significantly higher reactivity of palladium. Hence, palladium complexes for potential drug applications require strongly coordinating ligands to overcome this problem.

One such example of a palladium complex with strongly coordinating ligands is disclosed in a recent article, partly authored by some of present inventors (S. Aliwaini, A. J. Swarts, A. Blanckenberg, S. F. Mapolie and S. Prince, Biochem. Pharmacol., 2013, 86, 1650). This article reported a promising palladacycle complex, referred to therein as AJ5. Biological evaluation of AJ5 showed that it effectively inhibits proliferation of ME1402 and WM1158 melanoma cells with $IC_{50}$ values of 0.19 µM and 0.20 µM, respectively. Furthermore, AJ5 was evaluated against breast cancer cell lines, oestrogen receptor positive MCF7 and oestrogen receptor negative MDA-MB-231, as well as human breast cancer stem cells. The $IC_{50}$ values were found to be 0.175 µM and 0.193 µM for MCF-7 and MDA-MB-231, respectively. The mechanism of action against both cancers involves induction of apoptosis and autophagy. These findings suggested that AJ5 could be an effective chemotherapeutic agent.

However, a major problem with AJ5, as with many other metal-based drugs, is poor solubility, especially solubility in aqueous media. Since solubility is essential in the field of drug development, the aim was to design and synthesise binuclear palladacycles with improved solubility and activity.

SUMMARY OF THE INVENTION

According to a first aspect to the present invention there is provided a compound of the Formula (I)

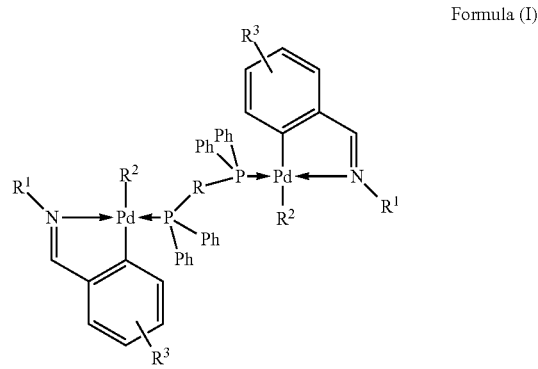

Formula (I)

or a stereoisomer, or pharmaceutically acceptable salt, hydrate, or solvate thereof wherein, $R^1$ is phenyl optionally substituted with one or more substituents independently selected from linear or branched $C_{1-4}$ alkyl, hydroxyl, and —$SO_3H$, $R^2$ is independently selected from halogen, —NCS, —SCN, $N_3$, and —$OOCCH_3$, and —$OS(CH_3)_2$, R is $(CH_2)_y$, wherein y is 1-3, $R^3$ is independently one or more substituents selected from hydrogen, and —$O(CH_2CH_2O)_xR^4$, provided that at least one $R^3$ is not hydrogen, wherein x is 1-3, $R^4$ is independently selected from hydrogen, —$CH_2CH_2OH$, and —$CH_2CH_2R^5$, a folic acid group, a monosaccharide group, a disaccharide group, and a fatty acid group, and $R^5$ is $C_{1-4}$ alkoxy.

In one embodiment, $R^1$ is phenyl optionally substituted with one or more substituents selected from $C_{1-4}$ alkyl.

In one embodiment, $R^1$ is phenyl substituted with two occurrences of isopropyl.

In one embodiment, $R^2$ is selected from Cl, Br, I, and F.

In one particular embodiment $R^2$ is Cl.

In one embodiment, $R^3$ is independently one or more substituents selected from —$O(CH_2)_2O(CH_2)_2OH$, —$O(CH_2)_2O(CH_2)_2$—$O(CH_2)_2OH$, —$O(CH_2)_2OH$, and —$O(CH_2)_2O(CH_2)_2O$ $CH_3$.

In another embodiment, $R^3$ is independently one or more —$O(CH_2)_2O$ $R^4$, wherein $R^4$ is independently selected from a folic acid group, a monosaccharide group, a disaccharide group, and a fatty acid group.

In one particular embodiment, the compound is:
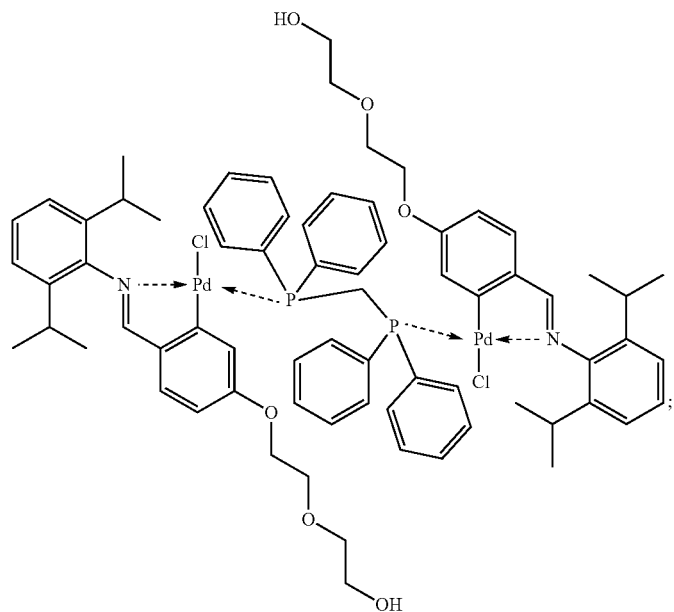
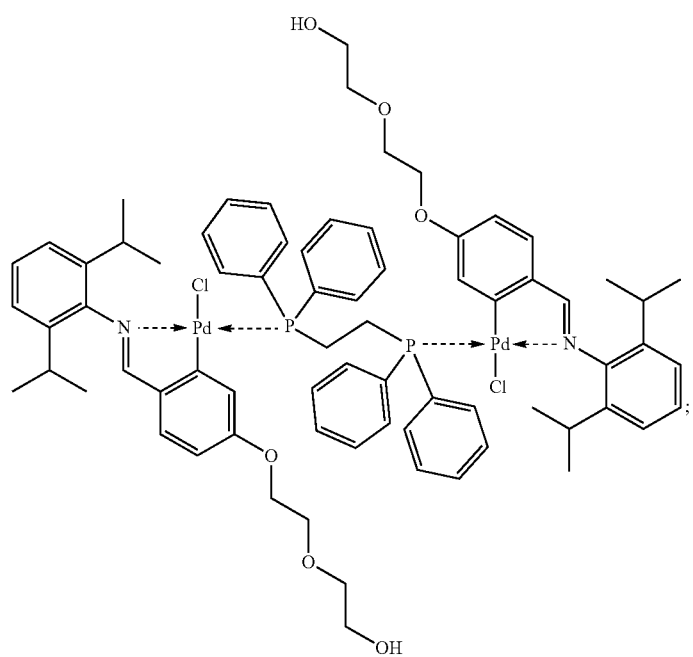

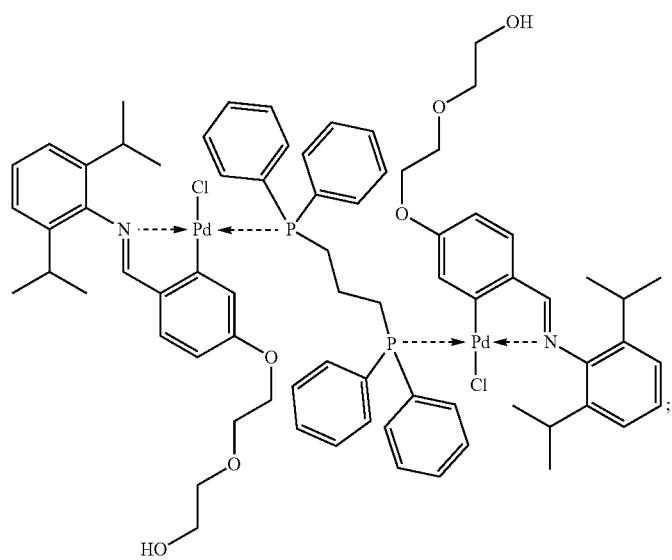
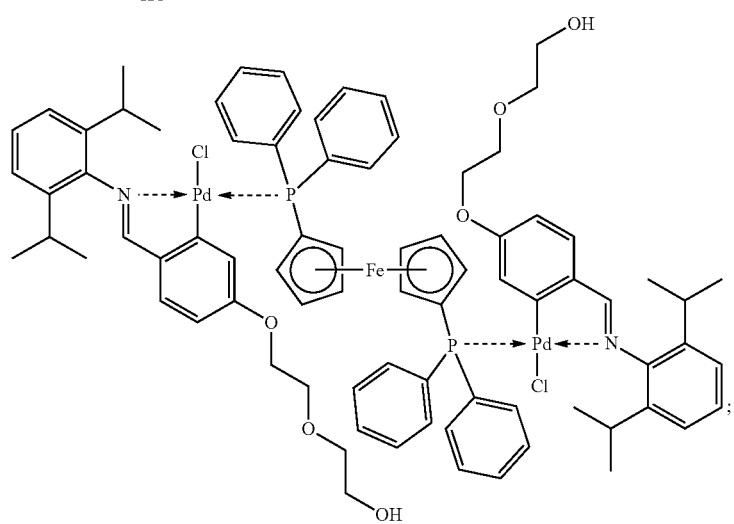
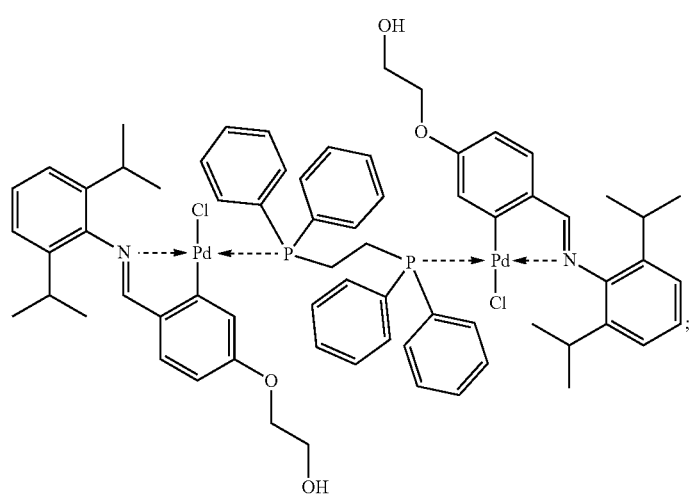

-continued
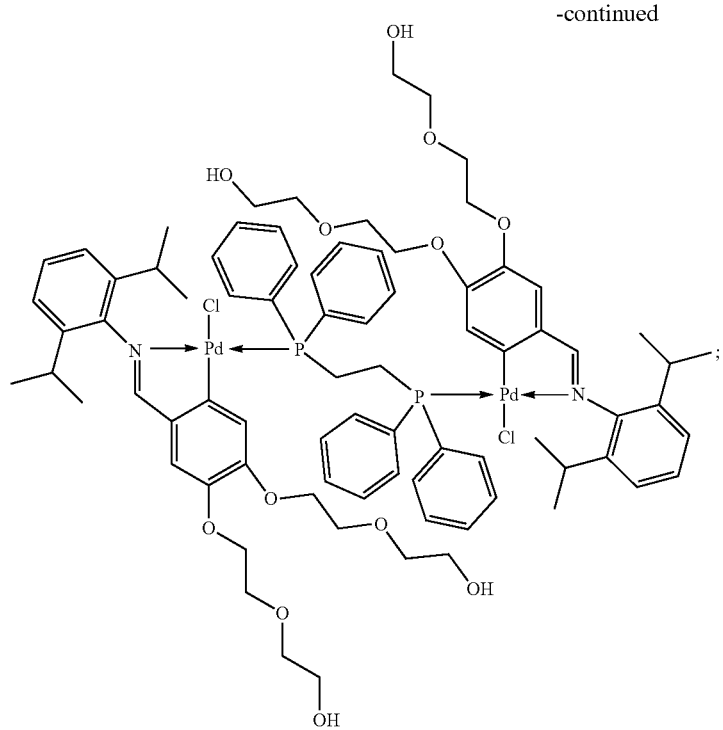
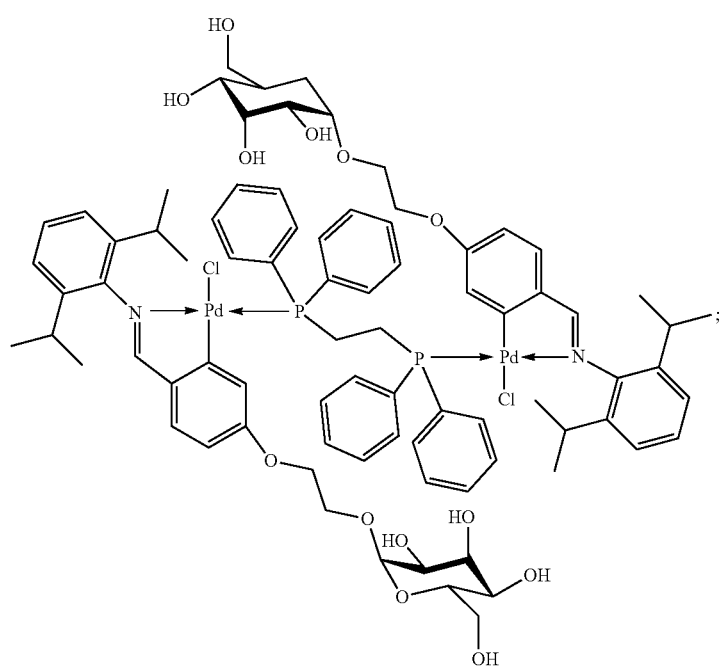

-continued
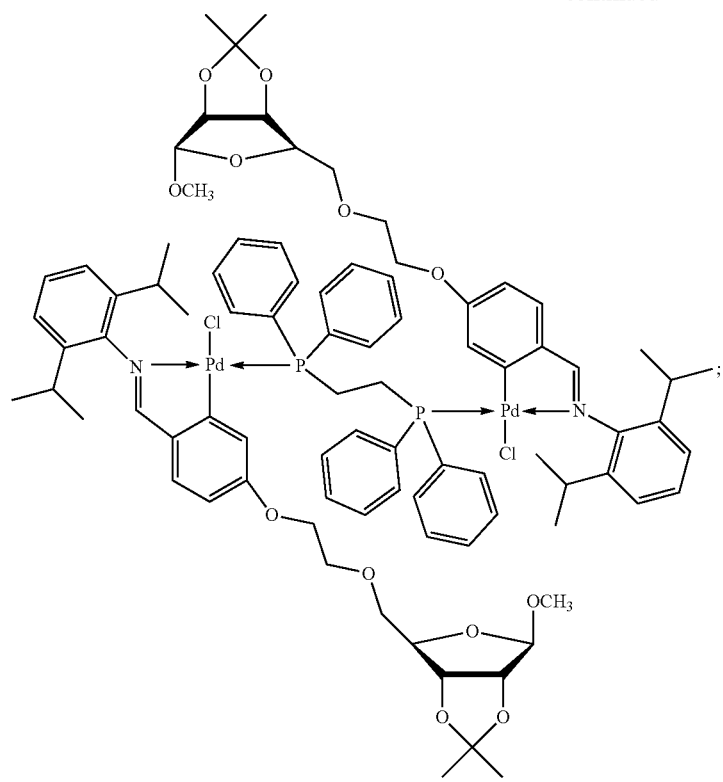
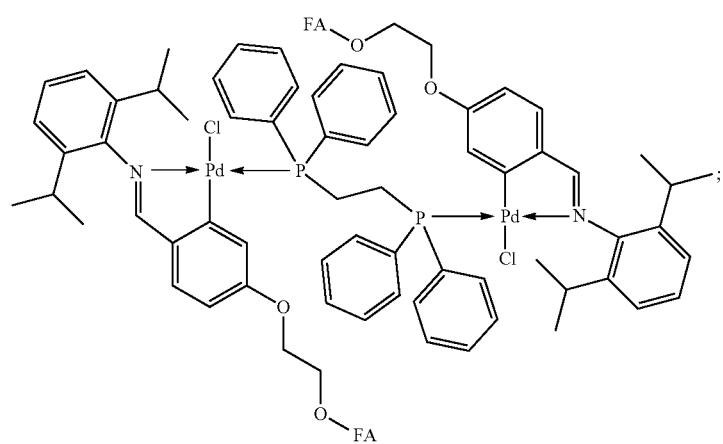
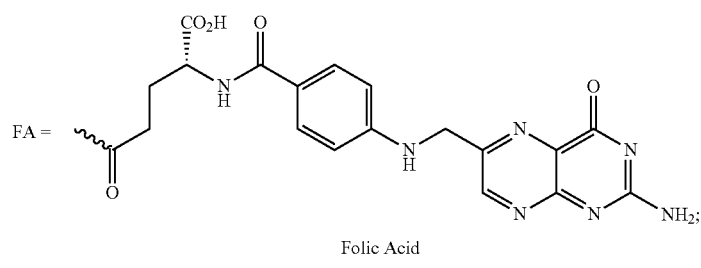

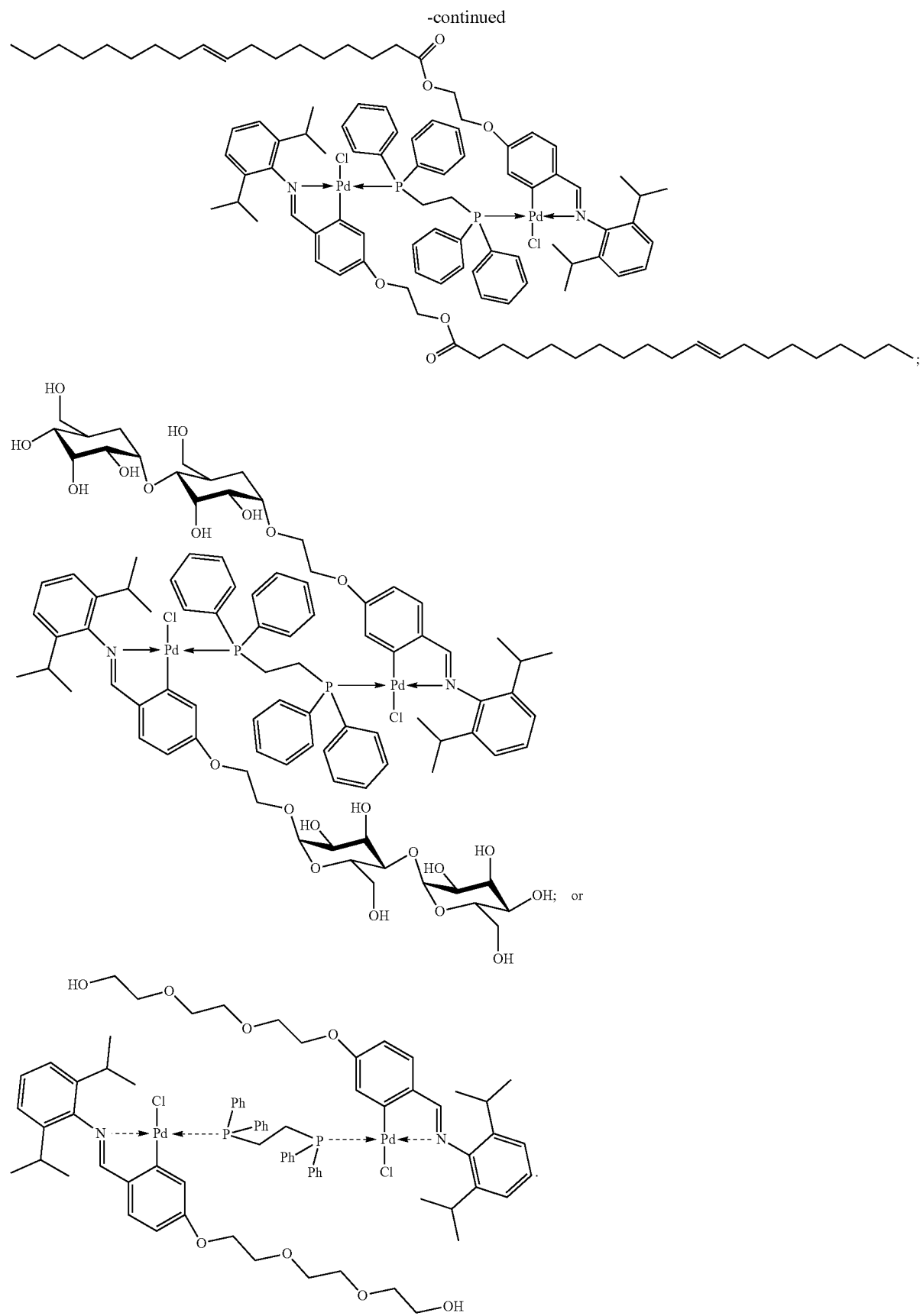

According to a second aspect to the present invention there is provided a pharmaceutical composition comprising a pharmaceutically acceptable carrier and a pharmaceutically effective amount of a compound of the invention.

In one embodiment, the composition comprises a further therapeutic agent.

According to a further aspect of the present invention there is provided for the use of a compound or a pharmaceutical composition of the invention as a medicament.

In one embodiment, there is provided for the use of a compound or a pharmaceutical composition of the invention in a method of treating a disease, the method comprising administering a pharmaceutically effective amount of the compound or composition to a subject in need thereof.

In one particular embodiment the disease is cancer.

In a particular embodiment the cancer is selected from breast cancer and skin cancer.

According to yet a further aspect of the present invention there is provided for the use of a compound of the invention in the preparation of e medicament for treating a disease, the treatment comprising administering a pharmaceutically effective amount of the medicament to a subject in need thereof.

In one particular embodiment, the disease is cancer.

In a particular embodiment, the cancer is selected from breast cancer and skin cancer.

According to yet a further aspect of the present invention there is provided for a method of treating a disease, the method comprising administering a compound or a pharmaceutical composition of the invention to a subject in need thereof.

In one particular embodiment, the disease is cancer.

In a particular embodiment, the cancer is selected from breast cancer and skin cancer.

BRIEF DESCRIPTION OF THE DRAWINGS

The invention will now be described in more detail with reference to the following non-limiting embodiments and figures in which:

FIG. 2 shows a table comprising $^1$H NMR data for substituted binuclear palladacycles BTC1-BTC4;

FIG. 5 shows a Western Blot analysis indicating cleaved PARP for BTC2, wherein UT=untreated.

DETAILED DESCRIPTION OF A PREFERRED EMBODIMENT

Figure 1:
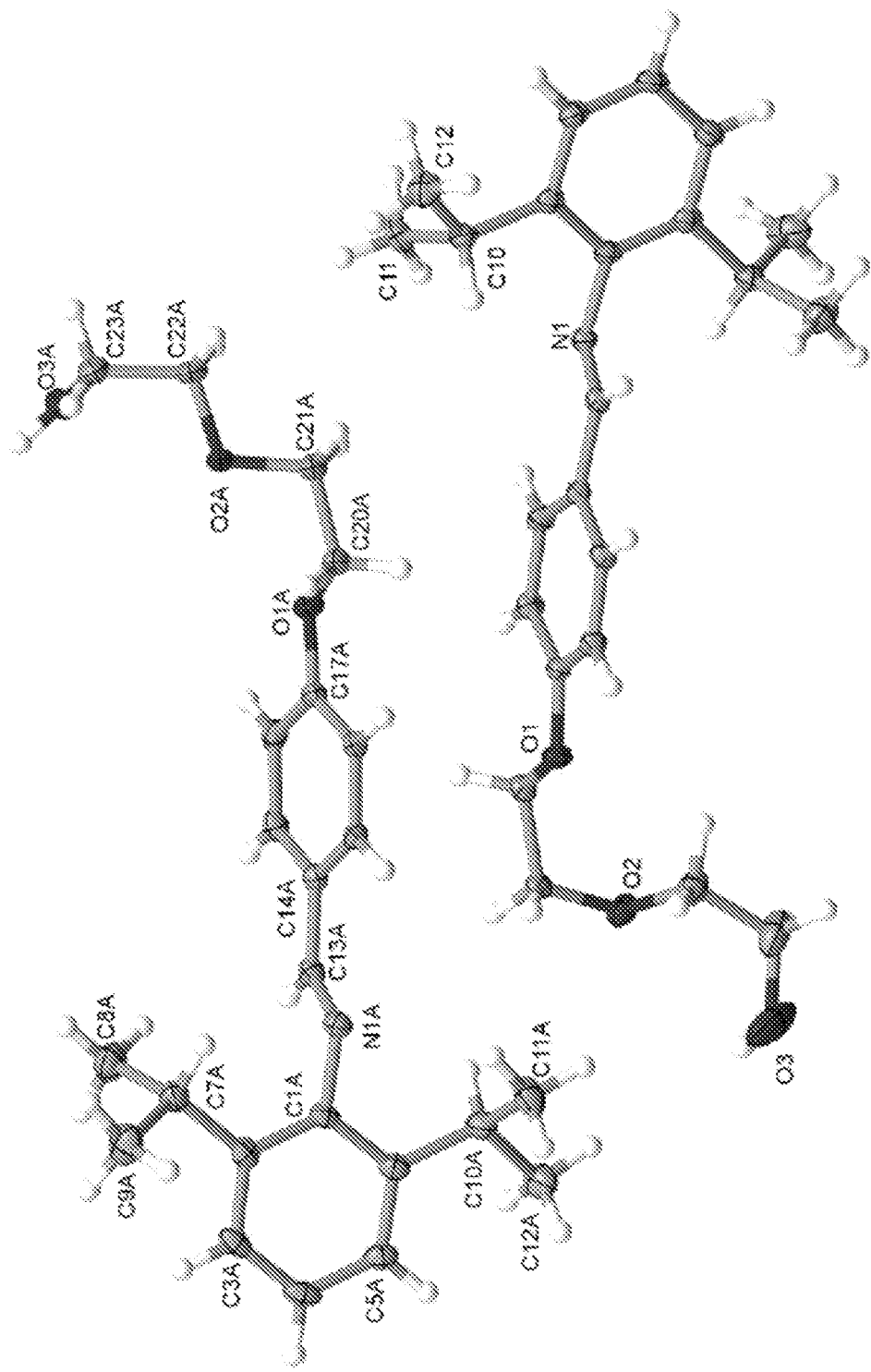
FIG. 1 shows the crystal structure of T2 as determined by single crystal X-ray diffraction.

The present invention will now be described more fully hereinafter with reference to the accompanying figures, in which some of the non-limiting embodiments of the invention are shown.

The invention as described hereinafter should not be construed to be limited to the specific embodiments disclosed, with slight modifications and other embodiments intended to be included within the scope of the invention.

Although specific terms are employed herein, they are used in a generic and descriptive sense only and not for purposes of limitation.

As used herein, throughout this specification and in the claims which follow, the singular forms "a", "an" and "the" include the plural form, unless the context clearly indicates otherwise.

The terminology and phraseology used herein is for the purpose of description and should not be regarded as limiting. The use of the terms "comprising", "containing", "having", "including", and variations thereof used herein, are meant to encompass the items listed thereafter, and equivalents thereof as well as additional items.

When describing the invention, which includes compounds, pharmaceutical compositions containing such compounds and methods of using such compounds and compositions, the following terms, if present, have the following meanings, unless otherwise indicated. It should also be understood that when described herein any of the moieties defined forth below may be substituted with a variety of substituents, and that the respective definitions are intended to include such substituted moieties within their scope as set out below. In this regard, unless otherwise stated, the term "substituted" is to be defined as set out below. It should be further understood that the terms "groups" and "radicals" can be considered interchangeable when used herein.

"Alkyl" means straight or branched aliphatic hydrocarbon with the number of carbon atoms specified. Particular alkyl groups have 1 to 8 carbon atoms. More particular is lower alkyl which has 1 to 6 carbon atoms. A further particular group has 1 to 4 carbon atoms. Exemplary straight chain groups include methyl, ethyl n-propyl, and n-butyl. Branched means that one or more lower alkyl groups such as methyl, ethyl, propyl or butyl is attached to a linear alkyl chain. Exemplary branched chain groups include isopropyl and iso-butyl.

"Alkoxy" refers to the group —OR$^5$ where R$^5$ is alkyl with the number of carbon atoms specified. Particular alkoxy groups are methoxy, ethoxy, n-propoxy, isopropoxy, n-butoxy, tert-butoxy, sec-butoxy, n-pentoxy, n-hexoxy, and 1,2-dimethylbutoxy. Particular alkoxy groups are lower alkoxy, i.e. with between 1 and 6 carbon atoms. Further particular alkoxy groups have between 1 and 4 carbon atoms.

"Alkylene" refers to divalent alkene radical groups having the number of carbon atoms specified, in particular having 1 to 6 carbon atoms and more particularly 1 to 4 carbon atoms which can be straight-chained or branched. This term is exemplified by groups such as methylene (—CH$_2$—), ethylene (—CH$_2$—CH$_2$—), or —CH(CH$_3$)— and the like.

"Alkenyl" refers to monovalent olefinically unsaturated hydrocarbon groups with the number of carbon atoms specified. Particular alkenyl has 2 to 8 carbon atoms, and more particularly, from 2 to 6 carbon atoms, which can be straight-chained or branched and having at least 1 and particularly from 1 to 2 sites of olefinic unsaturation. Particular alkenyl groups include ethenyl (—CH=CH$_2$), n-propenyl (—CH$_2$CH=CH$_2$), isopropenyl (—C(CH$_3$)=CH$_2$) and the like.

"Amino" refers to the radical —NH$_2$.

"Aryl" refers to a monovalent aromatic hydrocarbon group derived by the removal of one hydrogen atom from a single carbon atom of a parent aromatic ring system. In particular aryl refers to an aromatic ring structure, monocyclic or polycyclic, with the number of ring atoms specified. Specifically, the term includes groups that include from 6 to 10 ring members. Where the aryl group is a monocyclic ring system it preferentially contains 6 carbon atoms. Particularly aryl groups include phenyl, and naphthyl. The term "phenyl" and "Ph" is used interchangeably herein, unless indicated otherwise.

"Cycloalkyl" refers to a non-aromatic hydrocarbyl ring structure, monocyclic or polycyclic, with the number of ring atoms specified. A cycloalkyl may have from 3 to 10 carbon atoms, and in particular from 3 to 7 carbon atoms. Such cycloalkyl groups include, by way of example, single ring structures such as cyclopropyl, cyclobutyl, cyclopentyl, cyclohexyl, and cycloheptyl.

"Cyano" refers to the radical —CN.

"Halo" or "halogen" refers to fluoro (F), chloro (Cl), bromo (Br) and iodo (I). Particular halo groups are either fluoro or chloro.

"Hetero" when used to describe a compound or a group present on a compound means that one or more carbon atoms in the compound or group have been replaced by a nitrogen, oxygen, or sulfur heteroatom. Hetero may be applied to any of the hydrocarbyl groups described above such as alkyl, e.g. heteroalkyl, cycloalkyl, e.g. heterocycloalkyl, aryl, e.g. heteroaryl, and the like having from 1 to 4, and particularly from 1, 2 or 3 heteroatoms, more typically 1 or 2 heteroatoms, for example a single heteroatom.

"Heteroaryl" means an aromatic ring structure, monocyclic or fused polycyclic, that includes one or more heteroatoms independently selected from O, N and S and the number of ring atoms specified. In particular, the aromatic ring structure may have from 5 to 9 ring members. The heteroaryl group can be, for example, a five membered or six membered monocyclic ring or a fused bicyclic structure formed from fused five and six membered rings or two fused six membered rings or, by way of a further example, two fused five membered rings. Each ring may contain up to four heteroatoms typically selected from nitrogen, sulphur and oxygen. Typically, the heteroaryl ring will contain up to 4 heteroatoms, more typically up to 3 heteroatoms, more usually up to 2, for example a single heteroatom. In one embodiment, the heteroaryl ring contains at least one ring nitrogen atom. The nitrogen atoms in the heteroaryl rings can be basic, as in the case of an imidazole or pyridine, or essentially non-basic as in the case of an indole or pyrrole nitrogen. In general the number of basic nitrogen atoms present in the heteroaryl group, including any amino group substituents of the ring, will be less than five.

As used herein, the term "heterocycloalkyl" means a stable non-aromatic ring structure, monocyclic or polycyclic, that includes one or more heteroatoms independently selected from O, N and S. The non-aromatic ring structure may have from 4 to 10 ring members, and in particular from 4 to 7 ring members. A fused heterocyclic ring system may include carbocyclic rings and need only to include one heterocyclic ring. As used herein, the term "heterocycloalkenyl" means a "heterocycloalkyl", wherein one bond of the ring is reduced, thus the ring comprises a double bond.

"Hydroxyl" refers to the radical —OH, while "Oxo" refers to the radical =O.

"Substituted" refers to a group in which one or more hydrogen atoms are each independently replaced with the same or different substituent(s).

"Sulfo" or "sulfonic acid" refers to a radical such as —SO$_3$H. "Thiol" refers to the group —SH.

As used herein, term "substituted with one or more" refers to one to four substituents. In one embodiment it refers to one to three substituents. In further embodiments it refers to one or two substituents. In a yet further embodiment it refers to one substituent.

"Pharmaceutically acceptable" means approved or approvable by a regulatory agency such as the United States Food and Drug Administration agency, or any similar agency in countries other than the United States, or that is listed in the a generally recognized pharmacopoeia for use in animals, and more particularly in humans, such as the U.S. Pharmacopoeia.

"Pharmaceutically acceptable salt" refers to a salt of a compound of the invention that is pharmaceutically acceptable and that possesses the desired pharmacological activity of the parent compound. In particular, such salts are non-toxic may be inorganic or organic acid addition salts and base addition salts. Specifically, such salts include: (1) acid addition salts, formed with inorganic acids including: hydrochloric acid, hydrobromic acid, sulfuric acid, nitric acid, and phosphoric acid; or formed with organic acids including: acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo [2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, and muconic acid; or (2) salts formed when an acidic proton present in the parent compound either is replaced by a metal ion, e.g. an alkali metal ion, an alkaline earth ion, or an aluminum ion; or coordinates with an organic base including ethanolamine, diethanolamine, triethanolamine, and N-methylglucamine. Salts further include, by way of example only, sodium, potassium, calcium, magnesium, ammonium, and tetraalkylammonium; and when the compound contains a basic functionality, salts of non-toxic organic or inorganic acids, including hydrochloride, hydrobromide, tartrate, mesylate, acetate, maleate, and oxalate. The term 'pharmaceutically acceptable cation' refers to an acceptable cationic counter-ion of an acidic functional group. Such cations are exemplified by sodium, potassium, calcium, magnesium, ammonium, and tetraalkylammonium cations.

"Pharmaceutically acceptable vehicle" refers to a diluent, adjuvant, excipient or carrier with which a compound of the invention is administered.

"Prodrugs" refers to compounds, including derivatives of the compounds of the invention, which have cleavable groups and become by solvolysis or under physiological conditions the compounds of the invention which are pharmaceutically active in vivo. Such examples include, but are not limited to, choline ester derivatives and the like, N-alkylmorpholine esters and the like.

"Solvate" refers to forms of the compound that are associated with a solvent, usually by a solvolysis reaction. This physical association includes hydrogen bonding. Conventional solvents include, byway of example, water, ethanol, and acetic acid. The compounds of the invention may be prepared, for example, in crystalline form and may then be solvated or hydrated. Suitable solvates include pharmaceutically acceptable solvates, such as hydrates, and further include both stoichiometric solvates and non-stoichiometric solvates. In certain instances the solvate will be capable of isolation, for example when one or more solvent molecules are incorporated in the crystal lattice of the crystalline solid.

"Solvate" encompasses both solution-phase and isolable solvates. Representative solvates include hydrates, ethanolates and methanolates.

"Subject" includes humans. The terms "human", "patient" and "subject" are used interchangeably herein.

"Effective amount" means the amount of a compound of the invention that, when administered to a subject for treating a disease, is sufficient to effect such treatment for the disease. The "effective amount" can vary depending on the compound, the disease and its severity, and the age, weight, etc., of the subject to be treated.

"Treating" or "treatment" of any disease or disorder includes ameliorating the disease or disorder, i.e. arresting the disease or reducing the manifestation, extent or severity of at least one of the clinical symptoms thereof. In another embodiment "treating" or "treatment" refers to ameliorating at least one physical parameter, which may not be discernible by the subject. In yet another embodiment, "treating" or "treatment" refers to modulating the disease or disorder, either physically, (e.g. stabilization of a discernible symptom), physiologically, (e.g. stabilization of a physical parameter), or both. In a further embodiment, "treating" or "treatment" relates to slowing the progression of the disease.

Where ranges are referred to in this specification, for example $C_{1-4}$ alkyl, the citation of a range should be considered a representation of each member of the range.

It is also to be understood that compounds that have the same molecular formula but differ in the nature or sequence of bonding of their atoms or the arrangement of their atoms in space are termed "isomers". Isomers that differ in the arrangement of their atoms in space are termed "stereoisomers".

"Stereoisomers" that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S- sequencing rules of Cahn and Prelog, or by the manner in which the molecule rotates the plane of polarized light and designated as dextrorotatory or levorotatory (i.e. as (+) or (−)-isomers respectively). A chiral compound can exist as either individual enantiomer or as a mixture thereof. A mixture containing equal proportions of the enantiomers is called a "racemic mixture"'.

"Tautomers" refer to compounds that are interchangeable forms of a particular compound structure, and that vary in the displacement of hydrogen atoms and electrons. Thus, two structures may be in equilibrium through the movement of π electrons and an atom (usually H). For example, enols and ketones are tautomers because they are rapidly interconverted by treatment with either acid or base. Another example of tautomerism is the aci- and nitro- forms of phenylnitromethane, that are likewise formed by treatment with acid or base. Tautomeric forms may be relevant to the attainment of the optimal chemical reactivity and biological activity of a compound of interest.

The compounds of the invention may possess one or more asymmetric centers; such compounds can therefore be produced as individual (R)- or (S)-stereoisomers or as mixtures thereof. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art.

It will be appreciated by those skilled in the art that compounds of the invention may be metabolized to yield biologically active metabolites.

The present invention provides for novel binuclear palladacycle compounds that may be useful in the treatment of cancer, including breast cancer and skin cancer. The present invention also provides for methods for the production of these compounds, pharmaceutical compositions comprising these compounds, and methods for the treatment of cancer including the administration of these compounds or compositions, alone or in combination with further active agents.

According to a first aspect to the present invention there is provided a compound of the Formula (I)

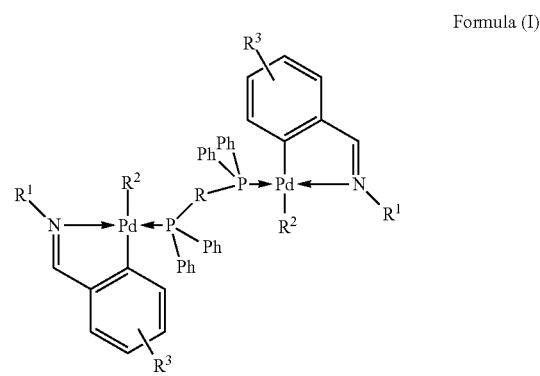

Formula (I)

or a stereoisomer, or pharmaceutically acceptable salt, hydrate, or solvate thereof.

In one embodiment of the invention, the $R^1$ substituent may be a phenyl group. Preferably, the phenyl group is substituted with one or more substituents which are independently selected from linear or branched $C_{1-4}$ alkyl, hydroxyl, and —$SO_3H$. In one embodiment, the $R^1$ substituent is substituted with two isopropyl groups, preferably $R^1$ is a 2,6-diisopropylaniline moiety. In an alternative embodiment, the $R^1$ substituent may be selected from other water-soluble moieties such as an aminophenol or sulfanilic acid.

In one embodiment, the $R^2$ substituents are independently selected from halogen, —NCS, —SCN, $N_3$, and —OOCCH$_3$, and —OS(CH$_3$)$_2$. In the embodiments wherein one or more of the $R^2$ groups is a halogen, the halogen may be selected from chlorine, bromine, iodine or fluorine. In one embodiment of the invention at least one $R^2$ is chlorine.

The group R, linking the phosphine atoms of the bisphosphine linker moiety in the compound, is defined by (CH$_2$)$_y$, with y being selected from 1, 2 or 3.

In one embodiment, the $R^3$ groups are independently one or more substituents selected from hydrogen, —O(CH$_2$)$_2$O (CH$_2$)$_2$OH, —O(CH$_2$)$_2$O(CH$_2$)$_2$O(CH$_2$)$_2$OH, —O(CH$_2$)$_2$OH, and —O(CH$_2$)$_2$O(CH$_2$)$_2$O CH$_3$, provided that at least one $R^3$ group is a group other than hydrogen. It will be appreciated that several variations and combinations of the $R^3$ substitution is possible. In a further embodiment, apart from the possible substituents referred to above, one or more of the $R^3$ groups may be a —O(CH$_2$)$_2$OR$^4$ group, wherein $R^4$ is selected from a folic acid group, a monosaccharide group, a disaccharide group, and a fatty acid group. It is anticipated that the introduction of these targeting species ($R^4$) into the $R^3$ moiety will further improve the transport of these compounds to the drug target.

In a further embodiment of the invention, the $R^4$ group is independently selected from hydrogen, and —CH$_2$CH$_2$R$^5$, wherein $R^5$ is $C_{1-4}$ alkoxy.

Exemplary compounds of the present invention may be represented by the chemical structures provided in the Table 1 below.

TABLE 1
Chemical structures of the compounds of the invention.
| Compound | Chemical Structure |
|---|---|
| 1 (BTC1) | 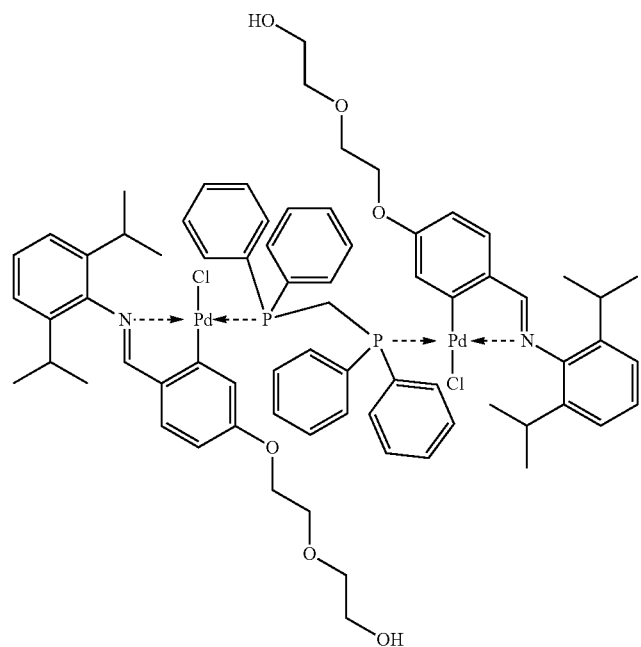 |
| 2 (BTC2) | 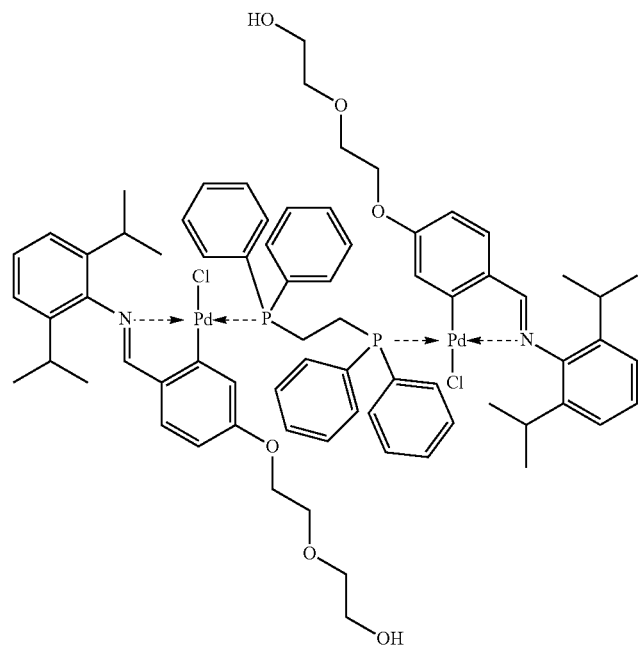 |

TABLE 1-continued
Chemical structures of the compounds of the invention.
| Compound | Chemical Structure |
|---|---|
| 3 (BTC3) | 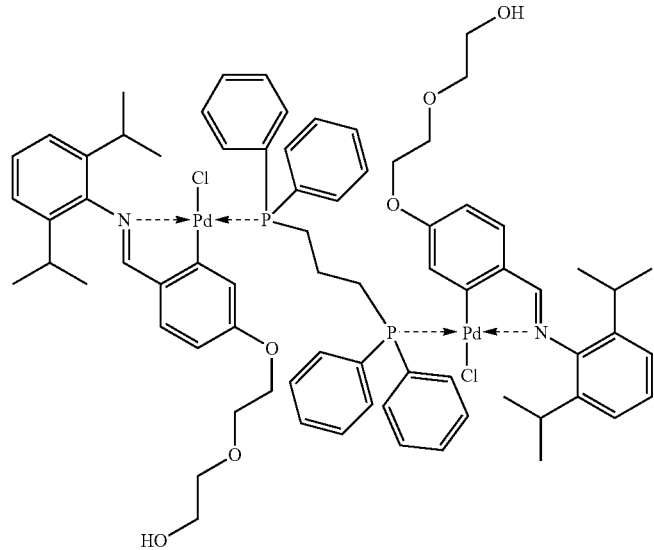 |
| 4 | 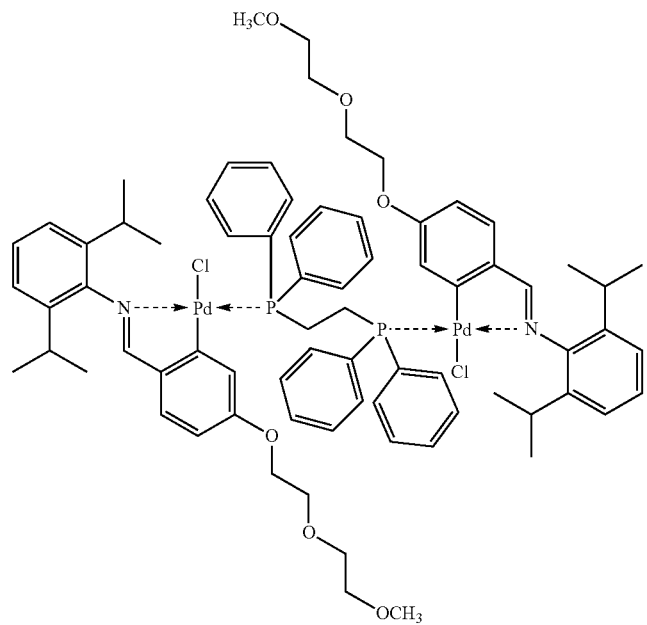 |

TABLE 1-continued
Chemical structures of the compounds of the invention.
| Compound | Chemical Structure |
|---|---|
| 5 (BTC5) | 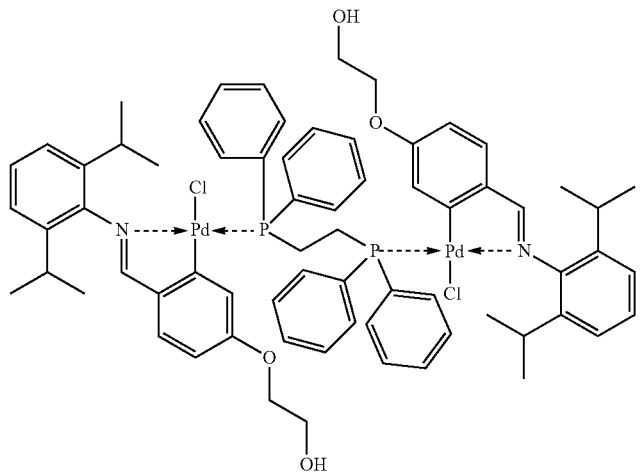 |
| 6 | 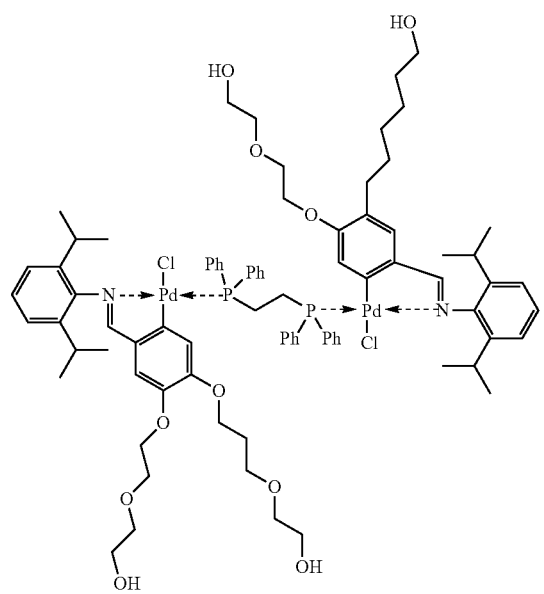 |
| 7 | 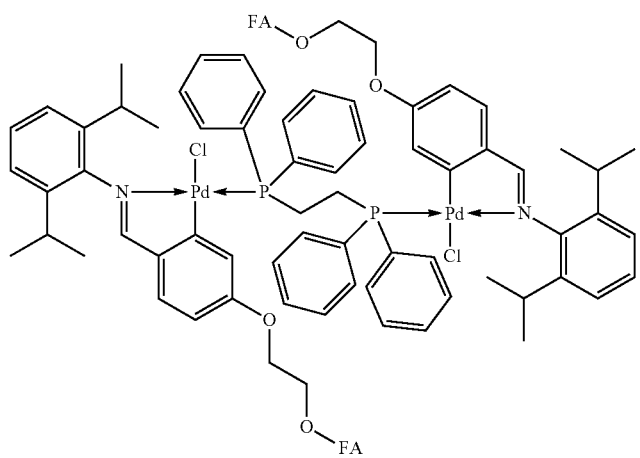 |

TABLE 1-continued
Chemical structures of the compounds of the invention.
| Compound | Chemical Structure |
|---|---|
|  | 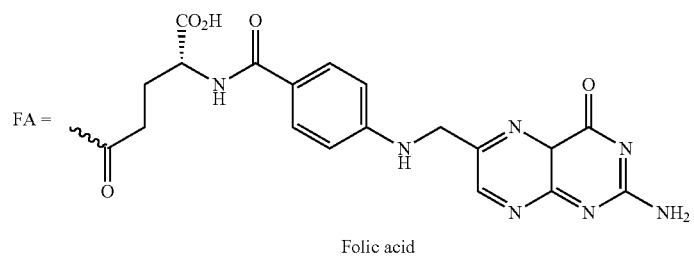
Folic acid |
| 8 | 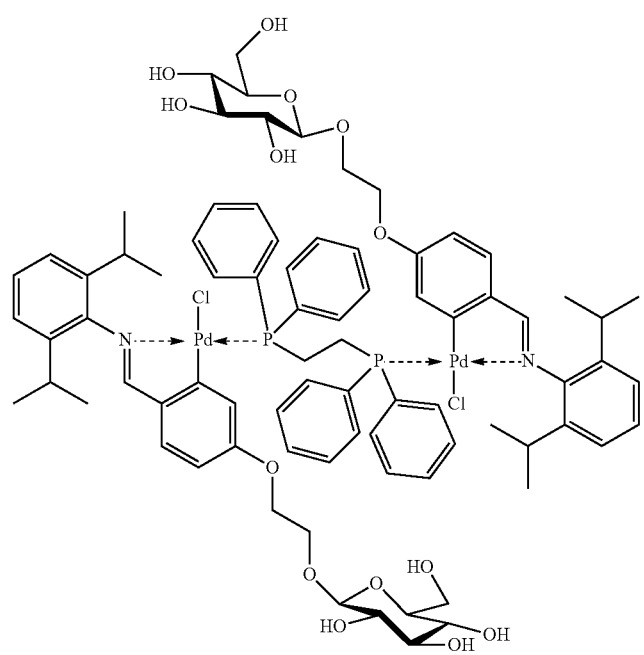 |
| 9 | 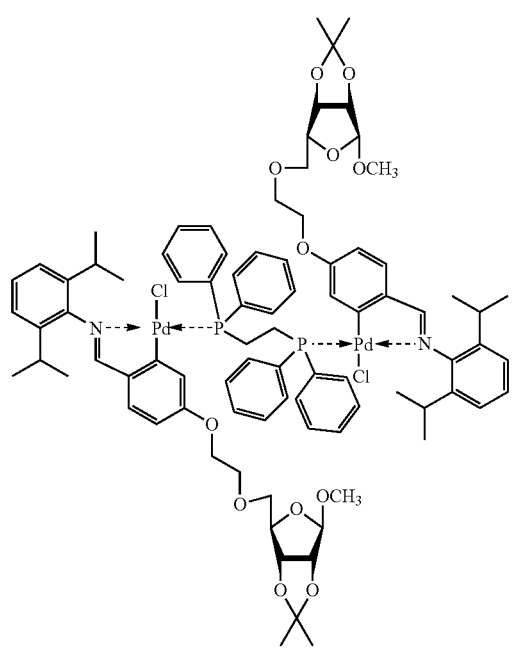 |

TABLE 1-continued
Chemical structures of the compounds of the invention.
| Compound | Chemical Structure |
|---|---|
| 10 | 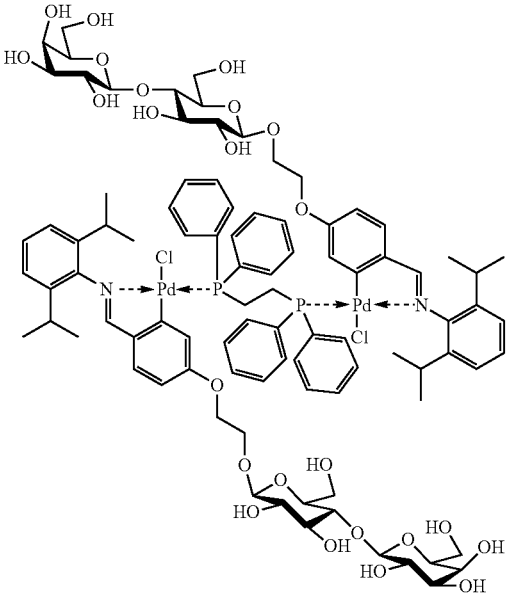 |
| 11 | 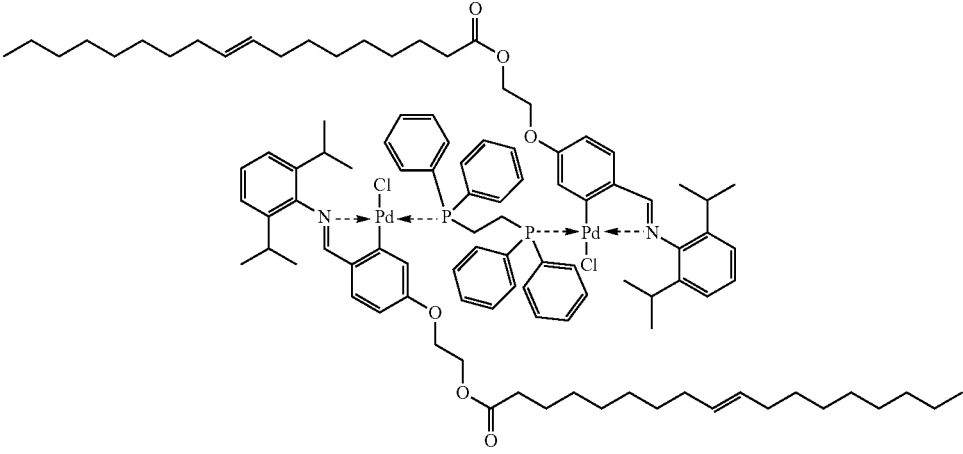 |
| 12 (BTC6) | 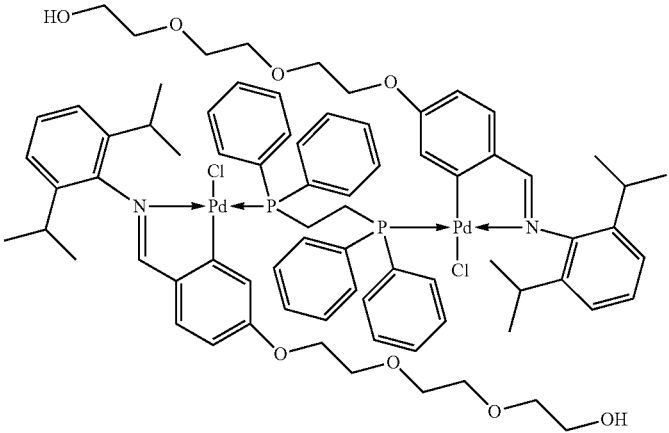 |

The synthesis of the compounds of the present invention is achieved by a four step process, as is shown in Scheme 1 below. In the final step of the synthesis procedure, the bisphosphine ligands, 1,1-bis(diphenylphosphino)methane (dppm), 1,2-bis(diphenylphosphino)ethane (dppe), 1,3-bis(diphenylphosphino)propane (dppp), and bis(diphenylphos-phino)ferrocene (dppf) were chosen to compare the effect of the aliphatic chain on activity and solubility.

All novel compounds were characterised by FT-IR and NMR ($^1$H, $^{13}$C and $^{31}$P) spectroscopy, mass spectrometry, micro analysis and melting point, and single crystal analysis, where applicable. In addition, the solubilities of the compounds were determined and analysed based on turbidimetric assay results.

Scheme 1: An exemplary synthesis of the tethered μ-bisphosphine palladacycles, wherein R is $CH_2$, $(CH_2)_3$, or $C_5H_4FrC_5H_4$.

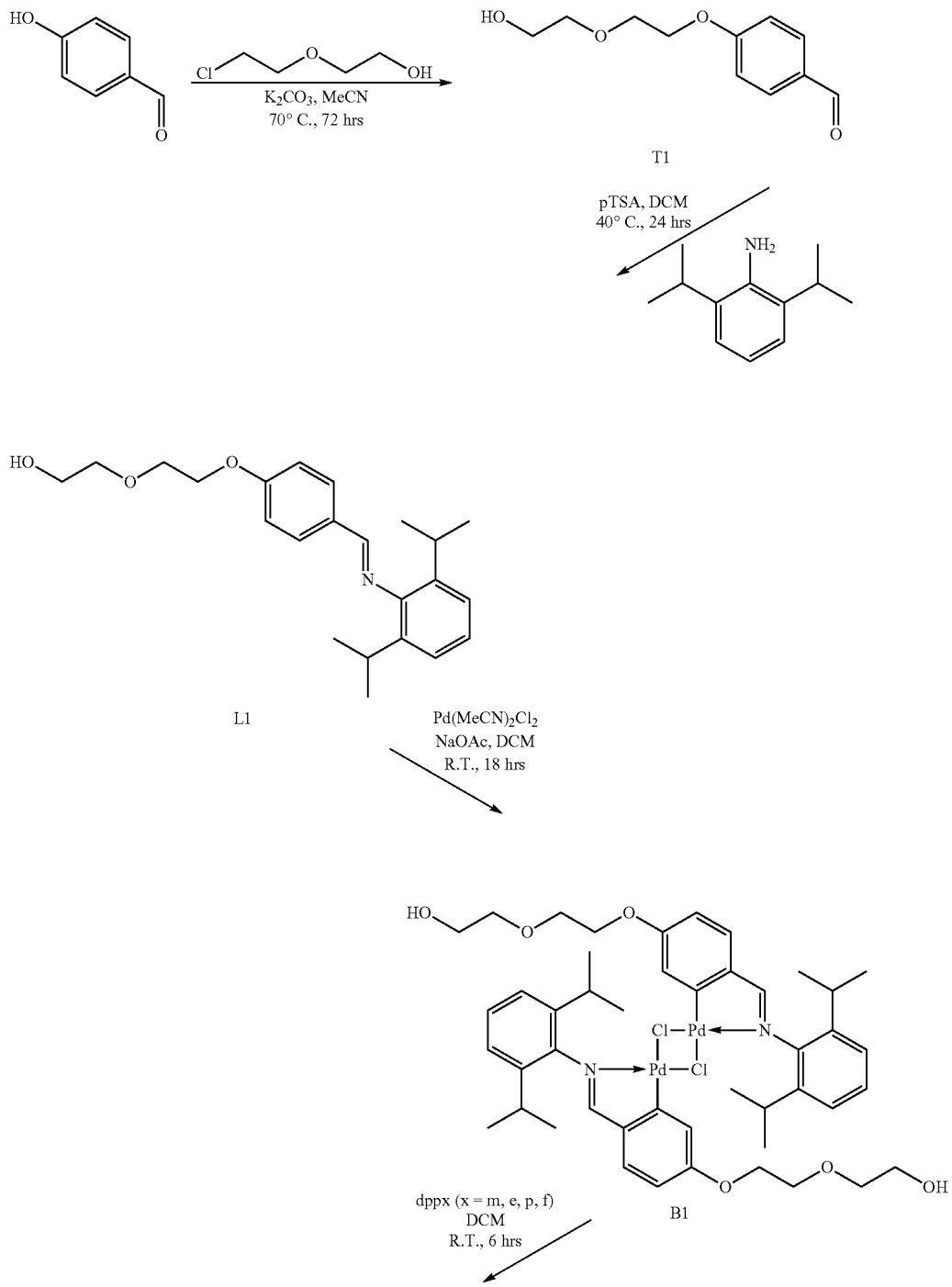

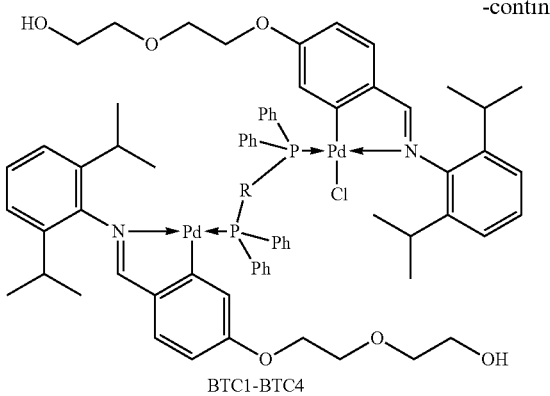

BTC1-BTC4

Functionalisation of 4-hydroxybenzaldehyde

Referring to Scheme 1 above, the functionalised aldehyde (T1) was synthesised by the method reported by Zhao et al. (Y. Zhao, Y. Li, Y. Li, C. Huang, H. Liu, S.-W. Lai, C.-M. Che and D. Zhu, Org. Biomol. Chem., 2010, 8, 3923-3927). 4-Hydroxybenzaldehyde was reacted with 2-(2-chloroethoxy)ethanol to form the functionalised aldehyde, 4-[2-(2-hydroxyethoxy)ethoxy]benzaldehyde (T1). The product was isolated as a pale orange oil in a fair yield. At low temperatures, the oil solidified to a pale orange solid.

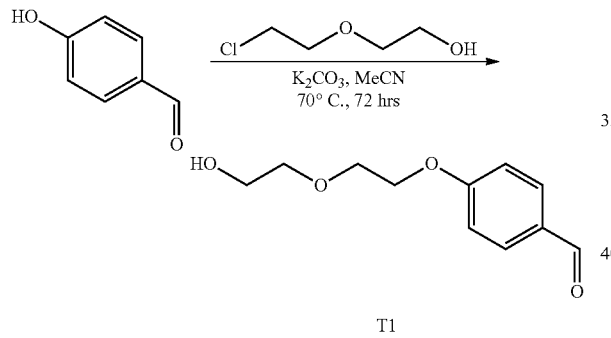

T1

Based on the results obtained in the preparation of the functionalised aldehyde (T1), it is expected that the method utilised in the preparation of T1 would be equally effective for the preparation of the aldehyde intermediates with other oligo ethylene glycol tethers as described herein. These aldehyde intermediates may be used, for example, in the preparation of compounds 4 to 6 and 12 shown in Table 1 above.

The synthesis of modified oligo ethylene glycol tethers, for example for use in the preparation of compounds 7 to 11 in Table 1 above can be achieved by synthetic methods known in the art. The conjugation of folic acid to ligand systems is known in the art, for example as provide in Li et al. (Lihua Li, Bing Xu Tetrahedron 2008, 64, 10986-10995) and Aronov et al. (O. Aronov, A. T. Horowitz, A. Gabizon, and D. Gibson, Bioconj. Chem. 2003. 14:3. 563-574). Methods for the conjugation of sugars to the metal complexes are also known in the art, for example in Ertl et al. (C. D. Ertl, F. Brunner, E. C. Constable, and C. E. Housecroft, J. Organomet. Chem. 2017, 849-850, 54-62). Based on the solubility and activity results obtained for BTC1-BTC3, comprising the tether systems as described, there is a fair technical expectation of positive solubility and activity results where these tether systems are further functionalised by the groups.

Preparation of Schiff Base Ligands

The Schiff base ligand (L1) synthesis was adapted from the method described by Mungwe et al. (N. Mungwe, A. J. Swarts, S. F. Mapolie and G. Westman, J. Organomet. Chem., 2011, 696, 3527-3535). The ligand was prepared by reacting 4-[2-(2-hydroxyethoxy)ethoxy]benzaldehyde (T1) with 2,6-diisopropylaniline in DCM. A catalyst was required for this reaction to occur; thus, para-toluene sulfonic acid (pTSA) was added and the reaction was heated to 40° C. The product was isolated as white needle crystals in a fair yield of approximately 60%.

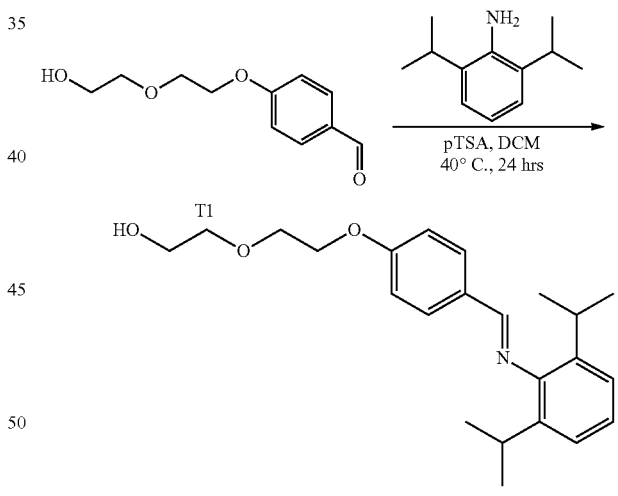

L1

FT-IR spectroscopy was used to determine whether the imine had been formed successfully. These findings were confirmed by $^1$H NMR spectroscopy, ESI-MS and elemental analysis. A single crystal was grown from DCM layered with hexane at low temperature (−16° C.). The crystal structure was determined by single crystal X-ray diffraction (FIG. 1).

Preparation of μ-Chloro Palladacycles

Cyclopalladation of the Schiff base ligand, via electrophilic C—H bond activation, was carried out to obtain the p-chloro bridged palladacycle. The synthesis was performed as described by Mungwe et al. as provided above, using two equivalents of Schiff base ligand, two equivalents of bis (acetonitrile)palladium dichloride and four equivalents of sodium acetate to form one equivalent of the palladacycle, B1. In this way B1, a yellow crystalline solid, was isolated in a high yield. The material was found to be sparingly soluble in DCM and DMSO. The product's structure was confirmed by FT-IR spectroscopy and ESI-MS. The use of other characterisation techniques was not possible due to the low solubility of the complex.

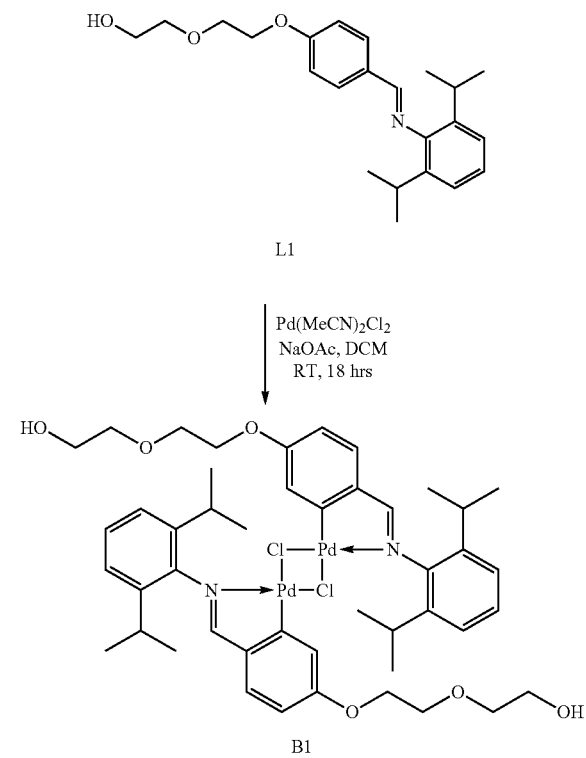

Preparation of the Bisphosphine-Bridged Palladacycles

With the µ-chloro bridged palladacycles in hand, the final synthetic step was to react these binuclear palladacycles with the various bisphosphines, to obtain the desired µ-bisphosphine-bridged palladacycles.

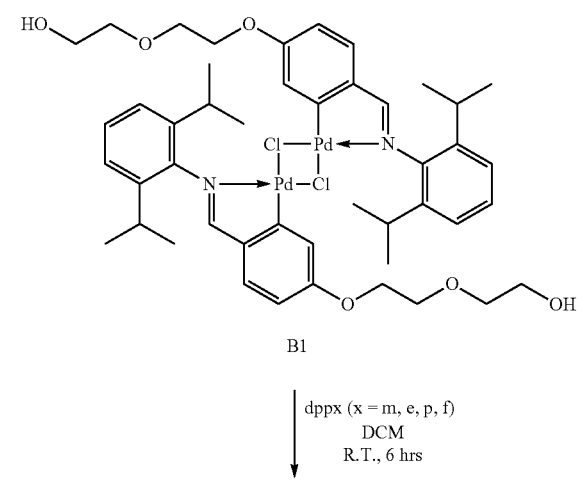

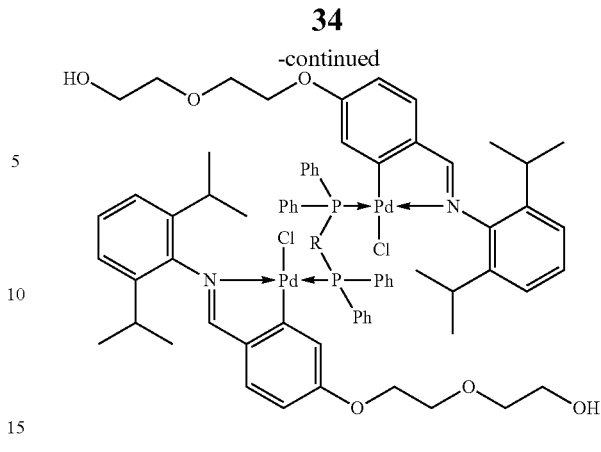

BTC1 - BTC4

Experimental Data

Synthesis of 4-[2-(2-Hydroxyethoxy)ethoxy]benzaldehyde (T1)

T1 was synthesised by stirring a solution of 4-hydroxybenzaldehyde (1.22 g, 10.0 mmol) in dry acetonitrile (75.0 mL) in a 2-neck round bottom flask. 2-(2-Chloroethoxy)ethanol (1.24 g, 10.0 mmol) was added to the solution, followed by potassium carbonate (6.50 g, 40.0 mmol). The resulting suspension was heated for 72 hours in an oil bath at ±70° C. The mixture was then cooled to room temperature and the solvent was removed under reduced pressure. The residue was dissolved in dichloromethane (100 mL) and the solution was washed with water (3×75 mL portions). The organic layer was dried over anhydrous magnesium sulphate after which the magnesium sulphate was removed by filtration. Solvent was removed from the filtrate to obtain an orange oily residue. The product was dried on high vacuum to remove any remaining solvent. Yield: 1.068 g, 65%. FT-IR ($v_{C=O}$, cm$^{-1}$) 1679; ($v_{C=O}$, cm$^{-1}$) 1254 (phenyl alkyl ether), 1046 (phenyl alkyl ether) and 1125 (aliphatic ether). $^1$H NMR (599.99 MHz, CDCl$_3$): δ 9.84 (s, 1H, CH=O); δ 7.78-7.81 (m, 2H, Ph); δ 6.98-7.00 (m, 2H, Ph); δ 4.19 (t, 2H, $^3J_{H-H}$ 4.7 Hz, Ph-OCH$_2$CH$_2$—); δ 3.87 (t, 2H, $^3J_{H-H}$ 4.7 Hz, Ph-OCH$_2$CH$_2$—); δ 3.74 (t, 2H, $^3J_{H-H}$ 4.7 Hz, —CH$_2$CH$_2$OH); δ 3.64-3.66 (m, 2H, —CH$_2$CH$_2$OH).

Synthesis of 4-[2-(2-Hydroxyethoxy)ethoxy]-2,6-diisopropylphenylamine (L1)

L1 was synthesised by stirring T1 (0.365 g, 1.74 mmol) in chloroform (10.0 mL). 2,6-Diisopropylaniline (0.327 mL, 1.74 mmol) was added, followed by a catalytic amount of pTSA (1 crystal). The solution was refluxed for 24 hours at ±55° C. The product was purified by column chromatography with 2:1 ethyl acetate/hexane as eluent. The product-containing fractions were combined and the solvent was removed. The residue was dissolved in DCM, the solution was concentrated and then layered with hexane at room temperature. Fine, white needle crystals formed and were isolated by vacuum filtration. The crystals were dried under vacuum. Yield: 0.404 g, 63%. FT-IR ($v_{C=O}$, cm$^{-1}$) 1630. m.p.: 89.8-94.5° C. $^1$H NMR (399.99 MHz, CDCl$_3$): δ 8.12 (s, 1H, CH=N); δ 7.85-7.87 (m, 2H, Ph); δ 7.15-7.17 (m, 2H, Ph); δ 7.08-7.12 (m, 1H, Ph); δ 7.04-7.07 (m, 2H, Ph); δ 4.23-4.25 (m, 2H, Ph-OCH$_2$CH$_2$—); δ 3.91-3.94 (m, 2H, Ph-OCH$_2$CH$_2$—); δ 3.78-3.82 (m, 2H, —CH$_2$CH$_2$OH); δ

3.70-3.72 (m, 2H, —CH$_2$CH$_2$OH); δ 2.94-3.04 (m, 2H, $^i$Pr—CH); δ 1.18 (d, 12H, $^3J_{H-H}$ 6.6 Hz, $^i$Pr—CH$_3$). $^{13}$C{$^1$H} NMR (CDCl$_3$, 599.99 MHz): δ 161.33 (C$_{Ar}$); δ 161.02 (CH=N); δ 149.38 (C$_{Ar}$); δ 137.77 (C$_{Ar}$); δ 130.19 (C$_{Ar}$); δ 129.34 (C$_{Ar}$); δ 123.88 (C$_{Ar}$); δ 122.94 (C$_{Ar}$); δ 114.80 (C$_{Ar}$); δ 72.61 (—CH$_2$CH$_2$OH); δ 69.51 (Ph-OCH$_2$CH$_2$—); δ 67.58 (Ph-OCH$_2$CH$_2$—); δ 61.77 (—CH$_2$CH$_2$OH); δ 28.48 ($^i$Pr—CH); δ 24.81 ($^i$Pr—CH$_3$); δ 23.10 ($^i$Pr—CH$_3$). ESI-MS: [M+H]$^+$ 370.2. Anal. Found: C, 72.0; H, 8.95; N, 3.46. Calc. for C$_{23}$H$_{31}$NO$_3$·0.9H$_2$O: C, 71.6; H, 8.57; N, 3.63.

Synthesis of [PdCl{4-[2-(2-hydroxyethoxy) ethoxy]}CH=N{2,6-$^i$Pr$_2$-C$_6$H$_3$}]$_2$ (T3)

T3 was synthesised by stirring a solution of bis(acetonitrile)palladium dichloride (0.100 g, 0.386 mmol) in acetonitrile (5.00 mL). T2 (0.142 g, 0.386 mmol) and sodium acetate (0.063 g, 0.77 mmol) were added to the solution. The resulting orange mixture was stirred for 18 hours in an oil bath at ±25° C. The solvent was removed to obtain a yellow oily residue which was dissolved in DCM (50.0 mL) and filtered through celite to remove any metallic palladium. The solvent volume was reduced and the solution was then layered with hexane at low temperature (−16° C.) to crystallise the product. The yellow crystalline solid was isolated by vacuum filtration and rinsed with hexane. The product was dried under vacuum. Yield: 0.156 g, 80%. FT-IR (v$_{C=N}$, cm$^{-1}$) 1597. m.p.: 150-154° C. ESI-MS: [M-Cl+2MeCN]$^+$ 1065; [(M/2)−Cl]$^{2+}$ 474.1. Anal. Found: C, 53.6; H, 5.98; N, 2.36. Calc. for C$_{46}$H$_{60}$Cl$_2$N$_2$O$_6$Pd$_2$: C, 54.1; H, 5.92; N, 2.74.

Synthesis of [(PdCl{4-[2-(2-hydroxyethoxy) ethoxy]}CH=N{2,6-$^i$Pr$_2$-C$_6$H$_3$})$_2$(μ-Ph$_2$PCH$_2$PPh$_2$)] (BTC1)

BTC1 was synthesised by stirring a solution of T3 (0.115 g, 0.113 mmol) in dichloromethane (5 mL) in a Schlenk tube. Dppm (0.043 g, 0.11 mmol) was added. The solution was stirred for 6 hours in an oil bath at ±25° C. The solvent volume was reduced by rotary evaporator to obtain a yellow oily residue. The product was recrystallised by layering the dichloromethane solution with hexane at low temperature. The solution was kept at low temperature (−16° C.) overnight. The off-white solid was isolated by vacuum filtration and rinsed with hexane. The recrystallisation was repeated and the crystals were dried under vacuum. Yield: 0.080 g, 50%. FT-IR (v$_{C=N}$, cm$^{-1}$) 1606. m.p.: 227-231° C. $^1$H NMR (299.74 MHz, CDCl$_3$): δ 8.14-8.20 (m, 8H, Ph); δ 7.89 (d, 2H, $^4J_{H-P}$ 7.9 Hz, CH=N); δ 7.15-7.31 (m, 20H, Ph); δ 6.47 (dd, 2H, $^3J_{H-H}$ 8.2 Hz and $^4J_{H-H}$ 2.2 Hz, Ph); δ 5.62-5.65 (m, 2H, Ph); δ 5.04-5.13 (m, 2H, —PCH$_2$P—); δ 3.66-3.67 (m, 4H, Ph-OCH$_2$—); δ 3.39-3.52 (m, 12H, Ph-OCH$_2$CH$_2$—, —CH$_2$CH$_2$OH and $^i$Pr—CH); δ 3.16-3.19 (m, 4H, —CH$_2$CH$_2$OH); δ 1.48 (d, 12H, $^3J_{H-H}$ 6.8 Hz, $^i$Pr—CH$_3$); δ 1.24 (d, 12H, $^3J_{H-H}$ 6.9 Hz, $^i$Pr—CH$_3$). $^{13}$C{$^1$H} NMR (CDCl$_3$, 75.38 MHz): δ 175.87 (CH=N); δ 161.96 (C$_{Ar}$—OCH$_2$CH$_2$—); δ 159.55 (—CCH=N—); δ 145.54 (o-metallated C); δ 141.21 (C$_{Ar}$); δ 140.33 (C$_{Ar}$); δ 135.44-135.61 (m, C$_{Ar}$); δ 130 (C$_{Ar}$); δ 129.93 (C$_{Ar}$); δ 128.02-128.17 (m, C$_{Ar}$); δ 126.98 (C$_{Ar}$); δ 122.86 (C$_{Ar}$); δ 122.38 (t, J$_{C-P}$ 5.1 Hz, C$_{Ar}$); δ 112.11 (C$_{Ar}$); δ 72.33 (—CH$_2$CH$_2$OH); δ 69.05 (Ph-OCH$_2$CH$_2$—); δ 66.68 (Ph-OCH$_2$CH$_2$—); δ 61.68 (—CH$_2$CH$_2$OH); δ 28.55 ($^i$Pr—CH); δ 24.70 ($^i$Pr—CH$_3$); δ 23.11 (—PCH$_2$P—). $^{31}$P{$^1$H} NMR (CDCl$_3$, 161.89 MHz): δ 34.39 (s). ESI-MS: [M-Cl]$^+$ 1369.34, [M−2Cl-Pd-T2]$^+$ 858.249, [M−2Cl-Pd-T2-{(Ph)$_2$PCH$_2$P(Ph)$_2$}+MeCN]$^+$ 474.127, [M−2Cl-Pd-T2-{(Ph)$_2$PCH$_2$P(Ph)$_2$}-C$_4$H$_9$O$_3$+MeCN]$^+$ 411.105. Anal. Found: C, 59.8; H, 5.87; N, 1.47. Calc. for C$_{71}$H$_{82}$Cl$_2$N$_2$O$_8$P$_2$Pd$_2$·H$_2$O: C, 59.9; H, 5.95; N, 1.97. Solubility: DMSO 2.85 mg/mL; 28% DMSO in water.

Synthesis of [(PdCl{4-[2-(2-hydroxyethoxy) ethoxy]}CH=N{2,6-$^i$Pr$_2$-C$_6$H$_3$})$_2$(μ-Ph$_2$P(CH$_2$)$_2$PPh$_2$)] (BTC2)

BTC2 was synthesised as above, using dppe as the bridging bis(phosphine) and the quantities as indicated: T3 (0.115 g, 0.113 mmol), dichloromethane (5.00 mL) and dppe (0.045 g, 0.11 mmol). Yield: 0.108 g, 68%. FT-IR (V$_{C=N}$, cm$^{-1}$) 1605. m.p.: 158-162° C. $^1$H NMR (599.99 MHz, CDCl$_3$): δ 7.88-7.89 (m, 2H, CH=N); δ 7.84-7.87 (m, 8H, Ph); δ 7.28-7.31 (m, 4H, Ph); δ 7.23-7.26 (m, 12H, Ph); δ 7.17 (d, 4H, $^3J_{H-H}$ 7.6 Hz, Ph); δ 6.47 (dd, 2H, $^3J_{H-H}$ 8.2 Hz and $^4J_{H-H}$ 2.3 Hz, Ph); δ 5.85-5.86 (m, 2H, Ph); δ 3.60-3.61 (m, 4H, Ph-OCH$_2$—); δ 3.34-3.42 (m, 12H, Ph-OCH$_2$CH$_2$—, —CH$_2$CH$_2$OH and $^i$Pr—CH); δ 3.11 (t, 12H, $^3J_{H-H}$ 4.7 Hz, —CH$_2$CH$_2$OH); δ 3.03 (br d, 4H, $^3J_{H-H}$ 2.3 Hz, —P(CH$_2$)$_2$P—); δ 1.32 (d, 12H, $^3J_{H-H}$ 7.0 Hz, $^i$Pr—CH$_3$); δ 1.17 (d, 12H, $^3J_{H-H}$ 7.0 Hz, $^i$Pr—CH$_3$). $^{13}$C{$^1$H} NMR (CDCl$_3$, 75.38 MHz): δ 175.61 (CH=N); δ 162.43 (C$_{Ar}$—OCH$_2$CH$_2$—); δ 159.86 (—CCH=N—); δ 145.09 (o-metallated C); δ 141.28 (C$_{Ar}$); δ 140.43 (C$_{Ar}$); δ 134.27-134.43 (m, C$_{Ar}$); δ 130.71 (C$_{Ar}$); δ 130.04 (C$_{Ar}$); δ 128.39-128.53 (m, C$_{Ar}$); δ 126.78 (C$_{Ar}$); δ 122.78 (C$_{Ar}$); δ 122.37-122.51 (m, JC—P, C$_{Ar}$); δ 112.23 (C$_{Ar}$); δ 72.33 (—CH$_2$CH$_2$OH); δ 69.05 (Ph-OCH$_2$CH$_2$—); δ 66.68 (Ph-OCH$_2$CH$_2$—); δ 61.68 (—CH$_2$CH$_2$OH); δ 28.55 ($^i$Pr—CH); δ 24.70 ($^i$Pr—CH$_3$); δ 23.11 (—P(CH$_2$)$_2$P—). $^{31}$P{$^1$H} NMR (CDCl$_3$, 161.89 MHz): δ 40.63 (s). ESI-MS: [M-Cl]$^+$ 1381.38; [M−2Cl-Pd-T2]$^+$ 872.266, [M−2Cl-Pd-T2-{(Ph)$_2$P(CH$_2$)$_2$P(Ph)$_2$}+MeCN]$^+$ 474.127, [M−2Cl-Pd-T2-{(Ph)$_2$P(CH$_2$)$_2$P(Ph)$_2$}-C$_4$H$_9$O$_3$+MeCN]$^+$ 411.105. Anal. Found: C, 59.6; H, 6.04; N, 1.55. Calc. for C$_{72}$H$_{84}$Cl$_2$N$_2$O$_8$P$_2$Pd$_2$·2H$_2$O: C, 59.4; H, 6.10; N, 1.93. Solubility: DMSO 32.6 mg/mL; 76% DMSO in water.

Synthesis of [(PdCl{4-[2-(2-hydroxyethoxy) ethoxy]}CH=N{2,6-$^i$Pr$_2$-C$_6$H$_3$})$_2$(μ-Ph$_2$P(CH$_2$)$_3$PPh$_2$)] (BTC3)

BTC3 was synthesised as above, using dppp as the bridging bis(phosphine) and the quantities as indicated: T3 (0.115 g, 0.113 mmol), dichloromethane (5.00 mL) and dppp (0.047 g, 0.11 mmol). Yield: 0.067 g, 42%. FT-IR (V$_{C=N}$, cm$^{-1}$) 1605. m.p.: 146-147° C. $^1$H NMR (599.99 MHz, CDCl$_3$): δ 7.91 (d, 2H, $^4J_{H-P}$ 7.6 Hz, CH=N); δ 7.77-7.80 (m, 8H, Ph); δ 7.39-7.41 (m, 4H, Ph); δ 7.31-7.33 (m, 8H, Ph); δ 7.25-7.28 (m, 4H, Ph); δ 7.19 (d, 4H, $^3J_{H-H}$ 7.6 Hz, Ph); δ 6.52 (dd, 2H, $^3J_{H-H}$ 8.2 Hz and 4J$_{H-H}$ 2.3 Hz, Ph); δ 5.98-6.00 (m, 2H, Ph); δ 3.66-3.68 (m, 4H, Ph-OCH$_2$—); δ 3.47-3.48 (m, 4H, Ph-OCH$_2$CH$_2$—); δ 3.43-3.45 (m, 4H, —CH$_2$CH$_2$OH); δ 3.31-3.38 (m, 4H, $^i$Pr—CH); δ 3.20-3.22 (m, 4H, —CH$_2$CH$_2$OH); δ 2.59-2.64 (m, 4H, —PCH$_2$CH$_2$CH$_2$P—); δ 1.60 (m, 2H, —PCH$_2$CH$_2$CH$_2$P—); δ 1.30 (d, 12H, $^3J_{H-H}$ 6.5 Hz, $^i$Pr—CH$_3$); δ 1.18 (d, 12H, $^3J_{H-H}$ 7.0 Hz, $^i$Pr—CH$_3$). $^{13}$C{$^1$H} NMR (CDCl$_3$, 100.57 MHz): δ 175.71 (CH=N); δ 162.23 (C$_{Ar}$—OCH$_2$CH$_2$—); δ 160.10 (t, J$_{C-P}$ 3.0 Hz, —CCH=N—); δ 145.47 (o-metallated C); δ 141.45 (C$_{Ar}$); δ 140.93 (C$_{Ar}$); δ 134.48-134.60 (m, C$_{Ar}$); δ 130.99 (C$_{Ar}$); δ 130.76 (C$_{Ar}$); δ 130.41 (C$_{Ar}$); δ 130.30 (C$_{Ar}$); δ 128.76-

128.86 (m, C$_{Ar}$); δ 127.08 (C$_{Ar}$); δ 123.03 (C$_{Ar}$); δ 122.78-122.89 (m, C$_{Ar}$); δ 112.39 (C$_{Ar}$); δ 72.61 (—CH$_2$CH$_2$OH); δ 69.32 (Ph-OCH$_2$CH$_2$—); δ 67.14 (Ph-OCH$_2$CH$_2$—); δ 61.97 (—CH$_2$CH$_2$OH); δ 28.74 ($^i$Pr—CH); δ 24.68 ($^i$Pr—CH$_3$); δ 23.48 (—PCH$_2$CH$_2$CH$_2$P—); δ 21.62 (—PCH$_2$CH$_2$CH$_2$P—). $^{31}$P{$^1$H} NMR (CDCl$_3$, 161.89 MHz): δ 35.46 (s). ESI-MS: [M-Cl]$^+$ 1397.37; [M-2Cl-Pd-T2]$^+$ 886.280, [M-2Cl-Pd-T2-{(Ph)$_2$P(CH$_2$)$_3$P(Ph)$_2$}+MeCN]$^+$ 474.127. Anal. Found: C, 59.6; H, 5.94; N, 1.47. Calc. for C$_{73}$H$_{86}$Cl$_2$N$_2$O$_6$P$_2$Pd$_2$·2H$_2$O: C, 59.7; H, 6.17; N, 1.91. Solubility: DMSO 76.0 mg/mL; 54% DMSO in water.

Synthesis of [(PdCl{4-[2-(2-hydroxyethoxy)ethoxy]}CH=N{2,6-$^i$Pr$_2$-C$_6$H$_3$})$_2$(μ-Ph$_2$P(C$_5$H$_4$)Fe(C$_5$H$_4$)PPh$_2$] (BTC4)

BTC4 was synthesised as above, using dppf as the bridging bis(phosphine) and the amounts as indicated here: T3 (0.115 g, 0.113 mmol), dichloromethane (5.00 mL) and dppf (0.063 g, 0.11 mmol). Yield: 0.115 g, 65%. FT-IR (v$_{C=N}$, cm$^{-1}$) 1605. m.p.: 87.5-89.4° C. $^1$H NMR (599.99 MHz, CDCl$_3$): δ 7.95 (d, 2H, $^4$J$_{H-P}$ 8.8 Hz, CH=N); δ 7.59-7.63 (m, 8H, Ph); δ 7.36-7.39 (m, 4H, Ph); δ 7.33-7.34 (m, 2H, Ph); δ 7.24-7.27 (m, 8H, Ph); δ 7.22 (d, 2H, $^3$J$_{H-H}$ 7.6 Hz, Ph); δ 7.16 (d, 4H, $^3$J$_{H-H}$ 7.3 Hz, Ph); δ 6.60 (dd, 2H, $^3$J$_{H-H}$ 8.2 Hz and $^4$J$_{H-H}$ 2.3 Hz, Ph); δ 6.03 (dd, 2H, J$_{H-H}$ 5.9 Hz and 2.34 Hz, Ph); δ 5.09 (br s, 4H, Cp ring); δ 4.42-4.43 (m, 4H, Cp ring); δ 3.68-3.70 (m, 4H, Ph-OCH$_2$—); δ 3.52-3.54 (m, 8H, Ph-OCH$_2$CH$_2$— and —CH$_2$CH$_2$OH); δ 3.36-3.43 (m, 4H, $^3$J$_{H-H}$, $^i$Pr—CH); δ 3.23 (br t, 4H, $^3$J$_{H-H}$ 4.7 Hz, —CH$_2$CH$_2$OH); δ 1.34 (d, 12H, $^3$J$_{H-H}$ 7.0 Hz, $^i$Pr—CH$_3$); δ 1.16 (d, 12H, $^3$J$_{H-H}$ 7.0 Hz, $^i$Pr—CH$_3$). $^{13}$C{$^1$H} NMR (CDCl$_3$, 75.38 MHz): δ 176.12 (CH=N); δ 161.58 (d, J$_{C-P}$ 2.2 Hz, C$_{Ar}$—OCH$_2$CH$_2$—); δ 159.62 (d, J$_{C-P}$ 5.5 Hz, —CCH=N—); δ 145.14 (o-metallated C); δ 141.30 (C$_{Ar}$); δ 140.83 (C$_{Ar}$); δ 134.34-134.50 (m, C$_{Ar}$); δ 132.46 (C$_{Ar}$); δ 131.79 (C$_{Ar}$); δ 130.56 (C$_{Ar}$); δ 130.32 (C$_{Ar}$); δ 127.89 (d, J$_{C-P}$ 10.5 Hz, C$_{Ar}$); δ 126.76 (C$_{Ar}$); δ 123.47 (d, J$_{C-P}$ 9.4 Hz, C$_{Ar}$); δ 122.67 (C$_{Ar}$); δ 112.17 (C$_{Ar}$); δ 76.91 (m, Cp ring); δ 75.72 (d, J$_{C-P}$ 8.06 Hz, Cp ring); δ 72.36 (—CH$_2$CH$_2$OH); δ 69.13 (Ph-OCH$_2$CH$_2$—); δ 66.68 (Ph-OCH$_2$CH$_2$—); δ 61.68 (—CH$_2$CH$_2$OH); δ 28.48 ($^i$Pr—CH); δ 24.81 ($^i$Pr—CH$_3$); δ 23.10 ($^i$Pr—CH$_3$). $^{31}$P{$^1$H} NMR (CDCl$_3$, 161.89 MHz): δ 31.38 (s). ESI-MS: [M-2Cl-Pd-T2]$^+$ 1028.23, [M-2Cl]$_2^+$ 752.179; [M-2Cl-Pd-T2-{(Ph)$_2$PC$_5$H$_4$FeC$_5$H$_4$P(Ph)$_2$}+MeCN]$_+$ 474.127. Solubility: DMSO 53.7 mg/mL; 98% DMSO in water.

Synthesis of 4-(2-hydroxyethoxy)benzaldehyde (T5)

4-Hydroxybenzaldehyde (1.22 g, 10.0 mmol), 2-chloroethanol (671 μL, 10.0 mmol) and K$_2$CO$_3$ (6.50 g, 40.0 mmol) was added to MeCN (75 mL). The reaction mixture was refluxed at 70° C. for 72 hours. During this time the reaction mixture turned pink and finally yellow. The solvent was removed with rotary evaporation to yield an off-white slurry. The slurry was dissolved with H$_2$O (50 mL) and the organic products extracted with DCM (3×30 mL). The combined organic fractions were dried over MgSO$_4$, filtered and the solvent removed. This yielded a light-yellow oil which hardened to an off-white solid under vacuum at 40° C. (689 mg, 40%). FTIR (ATR): 3362 cm$^{-1}$ (O—H stretch), 1674 cm$^{-1}$ (C=O stretch), 1252 cm$^{-1}$ (C—O stretch), 1214 cm$^{-1}$ (C—O stretch). $^1$H NMR (600 MHz, CDCl$_3$): δ (ppm)=9.88 (s, 1H, CH imine), 7.85-7.82 (dd, 2H, $^3$J=8.9 Hz, 2×CH Ar), 7.03-7.01 (dd, 2H, $^3$J=8.8 Hz, 2×CH Ar), 4.17 (t, 2H, $^3$J=4.6 Hz, ArOCH$_2$), 4.01 (t, 2H, $^3$J=4.5 Hz, CH$_2$OH), 2.19 (s, 1H, OH).

Synthesis of 4-(2-Hydroxyethoxy)-2,6-diisopropylphenylamine (L5)

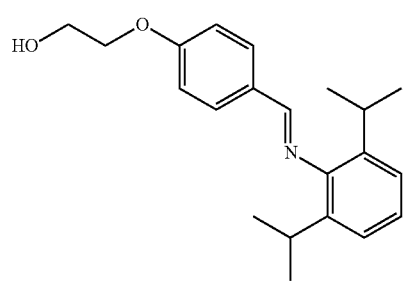

T5 (0.659 g, 3.97 mmol) was added to stirring chloroform (25 mL) followed by 2,6-diisopropylaniline (0.747 mL, 3.97 mmol) and a catalytic amount of p-toluene sulfonic acid (2 crystals). The clear brown solution was refluxed for 24 hours at 55° C. The solvent was removed to yield a brown oil which formed an off-white solid at room temperature. The solid was filtered off and recrystallized from dichloromethane:hexane to produce white crystals (260 mg, 83%). Mp: 143.7-144.1° C. FTIR (ATR): 3338 cm$^{-1}$ (O—H stretch), 1625 cm$^{-1}$ (C=N stretch). $^1$H NMR (400 MHz, CDCl$_3$): δ (ppm): 8.12 (s, 1H, HC=N), 7.88-7.85 (m, 2H, 2×CH Ar), 7.16-7.07 (m, 3H, 3×CH Ar), 7.06-7.02 (m, 2H, 2×CH Ar), 4.17 (t, 2H, $^3$J=4.6 Hz, CH$_2$), 4.01 (t, 2H, $^3$J=4.4 Hz, CH$_2$), 2.98 (hept., 2H, $^3$J=6.8 Hz, 2×CH), 2.08 (bs, 1H, OH), 1.17 (d, 12H, $^3$J=7.0 Hz, 4×CH$_3$). $^{13}$C NMR (151 MHz, CDCl$_3$): δ (ppm)=161.29, 160.96, 149.33, 137.74, 130.20, 129.42, 123.88, 122.93, 114.75 (9×CH Ar), 69.36, 61.33 (2×CH$_2$), 27.88 (2×CH), 23.45 (4×CH$_3$). ESI-MS: found: 326.2119 m/z [M+H]$^+$ (calc. 326.2120 m/z). EA: C$_{21}$H$_{27}$NO$_2$ Found (calc.): C: 78.00 (77.5), H: 8.34 (8.36), N: 4.24 (4.30).

Synthesis of [PdCl{4-(2-hydroxyethoxy)}CH=N{2,6-$^i$Pr-C$_6$H$_3$}]$_2$ (B5)

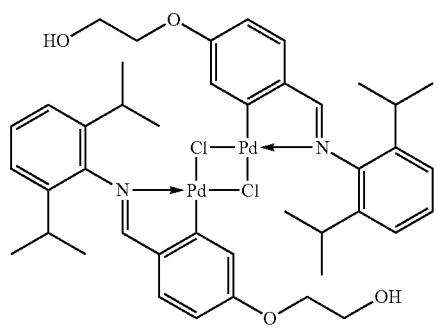

Pd(MeCN)$_2$Cl$_2$ (80 mg, 0.307 mmol) was added to stirring DCM (10 mL) at 25° C. and allowed to dissolve completely. L5 (100 mg, 0.307 mmol) was dissolved in a small amount of DCM and added to the Pd-precursor. NaOAc (50 mg, 0.615 mmol) was added to the reaction mixture. The reaction mixture was stirred at 25° C. for 18 hours. The reaction mixture was transferred to a round bottomed flask (50 mL) and the solvent removed under reduced pressure. The resulting yellow powder was dissolved in dichloromethane (c.a. 50 mL) and heated until fully dissolved. The solution was filtered through celite and the solvent volume reduced. The product was crystallized from a layered solution of dichloromethane:hexane at room temperature. Fine yellow crystals were obtained and dried under vacuum at 40° C. (95 mg, 66%). FTIR (ATR): 3392 cm$^{-1}$ (O—H stretch), 1592 (C=N stretch), 1263 (C—O stretch). $^1$H NMR (300 MHz, CDCl$_3$): δ (ppm)=7.62 (s, 1H, HC=N), 7.31-7.16 (m, 4H, 4×CH Ar), 6.70 (s, 1H, CH Ar), 6.62-6.59 (m, 1H, CH Ar), 4.02-3.93 (m, 4H, 2×CH$_2$), 3.56-3.48 (m, 2H, 2×CH), 1.96 (t, 1H, $^3$J=6.0 Hz, OH), 1.39 (d, 6H, $^3$J=5.9 Hz, 2×CH$_3$), 1.15 (d, 6H, $^3$J=7.2 Hz, 2×CH$_3$). $^{13}$C NMR (151 MHz, CDCl$_3$): δ (ppm)=175.12, 159.79, 158.25, 144.84, 142.17, 139.27, 129.68, 127.88, 123.54, 119.71, 111.80 (11×C Ar), 69.59, 61.63 (2×CH$_2$), 30.07, 28.58, 24.83, 23.39 (2×CH, 2×CH$_3$). ESI-MS: found: 471.1281 m/z [M−Cl−H]$^+$ (calc. 471.071 m/z), found: 897.1673 m/z [M−Cl]$^+$ (calc. 897.1702 m/z). EA: C$_{42}$H$_{52}$Cl$_2$Pd$_2$N$_2$O$_4$. Found (calc.): C: 53.97 (54.09), H: 5.64 (5.62), N: 2.91 (3.00).

Synthesis of [(PdCl{4-(2-hydroxyethoxy})CH=N{2,6-$^i$Pr$_2$-C$_6$H$_3$})$_2$(μ-Ph$_2$P(CH$_2$)$_2$PPh$_2$)] (BTC5)

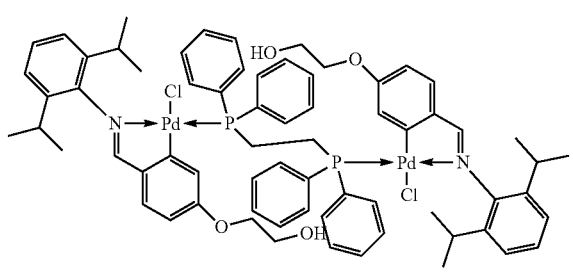

BTC5

B5 (100 mg, 0.107 mmol) was added to DCM (10 mL) at 25° C. The bridge was not fully soluble, so the dppe (43 mg, 0.107 mmol) was added to the solution. With the addition of the phosphine, the bridge dissolved fully to form a clear yellow solution. After 3 hours a pale-yellow precipitate started to form. After 6 hours the reaction was stopped, and the solvent removed with rotary evaporation. The compound was dissolved in DCM (ca. 40 mL) and heated. The solution was layered with hexane at room temperature to yield a pale-yellow static powder, which was filtered off and dried under vacuum (96 mg, 68%). Mp: 211° C. (decomposed to brown), 216° C. (brown to black). FTIR (ATR): 3594 cm$^{-1}$ (O—H stretch), 1603 cm$^{-1}$ (C=N stretch). $^1$H NMR (600 MHz, CDCl$_3$): δ (ppm)=7.92 (t, 1H, 4J=3.9 Hz, HC=N), 7.86-7.83 (m, 4H, 4×CH Ar dppe), 7.32 (t, 2H, $^3$J=7.3 Hz, 2×CH Ar), 7.28-7.25 (m, 6H, 6×CH Ar dppe), 7.19 (d, 2H, $^3$J=7.6 Hz, 2×CH Ar), 6.49 (dd, 1H, $^3$J=8.2 Hz, 4J=2.4 Hz, CH Ar), 5.90 (m, 1H, CH Ar), 3.50 (m, 2H, CH$_2$ tether), 3.42 (hept., 2H, 2×CH), 3.14 (t, 2H, $^3$J=4.6 Hz, CH$_2$ tether), 3.11 (m, 2H, CH$_2$ dppe), 1.67 (t, 1H, $^3$J=6.3 Hz, OH), 1.35 (d, 6H, $^3$J=7.1 Hz, 2×CH$_3$), 1.20 (d, 6H, $^3$J=6.9 Hz, 2×CH$_3$). $^{13}$C NMR (151 MHz, CDCl$_3$): δ (ppm)=175.73 (HC=N), 162.51, 160.10, 145.23, 141.40, 140.25, 134.39 (t, J$_{C-P}$), 130.99, 130.85, 130.68, 130.23, 128.61 (t, J$_{C-P}$), 126.97, 122.95, 112.01, 68.67 (CH$_2$), 61.05 (CH$_2$), 29.85, 28.69, 25.30 (t, J$_{C-P}$), 24.59, 23.28. $^{31}$P NMR (162 MHz, CDCl$_3$): δ (ppm)=40.10 (dppe). ESI-MS: found: 471.1281 m/z [M−Cl−H]$^+$ (calc. 471.071 m/z), found: 897.1673 m/z [M−C]$^+$ (calc. 897.1702 m/z). EA: C$_{68}$H$_{76}$Cl$_2$N$_2$O$_4$P$_2$Pd$_2$. Found (calc.): C: 61.20 (61.36), H: 5.43 (5.75), N: 2.08 (2.10).

Synthesis of [4-(2-[2-(2-hydroxyethoxy)ethoxy]ethoxy)benzaldehyde] (T6)

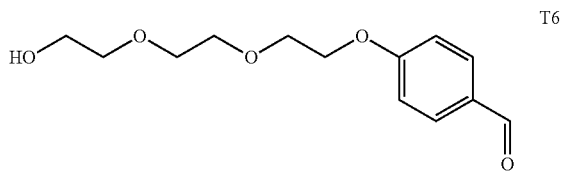 [SMILES: O=Cc1ccc(OCCOCCOCCO)cc1]

T6

4-Hydroxybenzaldehyde (1.22 g, 10.0 mmol), 2-(2-(2-chloroethoxy) ethoxy)- ethanol (1.48 mL, 10.0 mmol) and K$_2$CO$_3$ (6.50 g, 40.0 mmol) was added to MeCN (75 mL). The reaction mixture was refluxed at 70° C. for 72 hours. The solvent was removed with rotary evaporation to yield an off-white slurry. The slurry was dissolved with H$_2$O (50 mL) and the organic products extracted with DCM (3×30 mL). The combined organic fractions were dried over MgSO$_4$, filtered and the solvent removed. The resulting yellow-brown oil was dried under vacuum for 9 hours (0.9 g, 35%). FTIR (ATR): 3423 cm$^{-1}$ (O—H stretch), 1680 cm$^{-1}$ (C=O stretch), 1251 cm$^{-1}$ (C—O stretch), 1212 cm$^{-1}$ (C—O stretch). $^1$H NMR (300 MHz, CDCl$_3$): δ (ppm)=9.84 (s, 1H, HC=O), 7.80-7.78 (dd, 2H, $^3$J=8.9 Hz, 4J=2.5 Hz, 2×CH Ar), 7.00-6.98 (dd, 2H, $^3$J=8.9 Hz, 4J=2.5 Hz, 2×CH Ar), 4.19 (t, 2H, $^3$J=4.6 Hz, CH$_2$), 3.86 (t, 2H, $^3$J=5.1, CH$_2$), 3.74-3.65 (m, 11H), 3.61 (t, 1H, $^3$J=6.0 Hz, OH), 3.58 (t, 3H, $^3$J=4.5 Hz). The product was used without further purification.

Synthesis of 4-{2-[2-(2-hydroxyethoxy)ethoxy]ethoxy})-2,6-diisopropylphenylamine (L6)

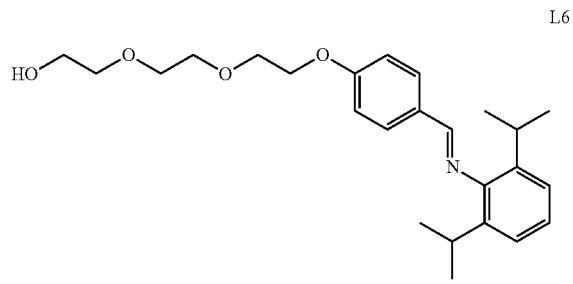 [SMILES: CC(C)c1cccc(C(C)C)c1/N=C/c1ccc(OCCOCCOCCO)cc1]

L6

T6 (1.750 g, 6.88 mmol) was stirred in chloroform (25 mL) to which 2,6-diisopropylaniline (1.30 mL, 6.88 mmol) was added, followed by a catalytic amount of pTSA (2 crystals). The clear orange-brown solution was refluxed for 48 hours at 55° C. The solvent was removed to yield a brown oil. The oil was purified with column chromatography (EtOAc:Hex 2:1) and fractions of c.a. 5 mL were collected. The relevant fractions were collected, and the solvent removed to yield a white powder (498 mg, 35%). Mp: 55.2-55.9° C. FTIR (ATR): 1625 cm$^{-1}$ (HC=N stretch), 1112 cm$^{-1}$ (C—O stretch), 1068 cm$^{-1}$ (C—O stretch), 1053 cm$^{-1}$ (C—O stretch). $^1$H NMR (600 MHz, CDCl$_3$): δ (ppm)=8.10 (s, 1H, HC=N), 7.85 (dd, 2H, $^3$J=8.8 Hz, 2×CH Ar), 7.15 (d, 2H, $^3$J=7.9 Hz, 2×CH Ar), 7.09 (dd, 2H, $^3$J=8.4 Hz, 4J=6.9 Hz, CH Ar), 7.03 (d, 2H, $^3$J=8.7 Hz, 2×CH Ar), 4.23-4.22 (m. 2H, CH$_2$), 3.92-3.90 (m, 2H, CH$_2$), 3.77-3.72 (m, 6H, 3×CH$_2$), 3.65-3.63 (m, 2H, CH$_2$), 2.98 (hept., 2H, $^3$J=6.9 Hz, 2×CH), 2.36 (t, 1H, $^3$J=6.2 Hz, OH), 1.16 (d, 12H, $^3$J=6.9 Hz, 4×CH$_3$). $^{13}$C NMR (151 MHz, CDCl$_3$): δ (ppm)=161.54, 161.20, 149.58, 137.94, 130.33, 129.43, 124.02, 123.10, 114.98 (9×CH Ar), 72.64, 71.05, 70.54, 69.77, 67.72, 61.94 (6×CH$_2$), 28.05 (2×CH), 23.63 (4×CH$_3$). ESI-MS: found: 414.2639 m/z [M+H]$^+$ (calc. 414.2644 m/z), found: 436.2453 m/z [M+Na]$^+$ (calc. 436.2464 m/z). EA: C$_{25}$H$_{35}$NO$_4$·0.5H$_2$O. Found (calc.): C: 71.13 (71.06), H: 8.60 (8.59), N: 3.20 (3.31).

Synthesis of [PdCl{4-{2-[2-(2-hydroxyethoxy)ethoxy]ethoxy})}CH=N{2,6-$^i$Pr-CH$_3$}]$_2$ (B6)

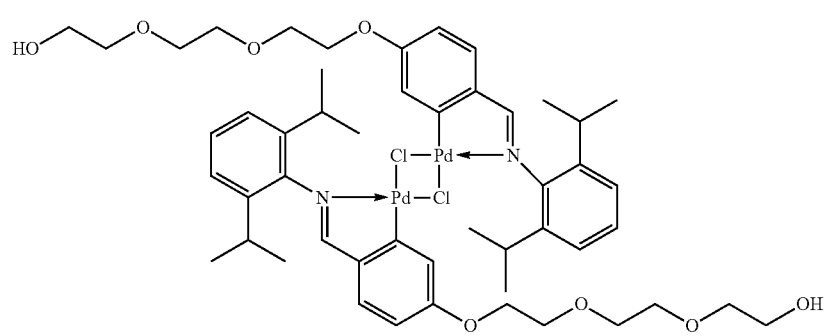

B6

Pd(MeCN)$_2$Cl$_2$ (50 mg, 193 mmol) was added to stirring DCM (10 mL) at 25° C. and allowed to dissolve completely. Lδ (80 mg, 0.193 mmol) was dissolved in a small amount of DCM and added to the Pd-precursor. NaOAc (32 mg, 0.387 mmol) was added to the reaction mixture. The reaction mixture was stirred at 25° C. for 18 hours. The reaction mixture was transferred to a round bottomed flask (50 mL) and the solvent removed under reduced pressure. The resulting yellow oil was dissolved in DCM (c.a. 20 mL). The solution was filtered through celite, washed with DCM (ca. 20 mL) and the solvent removed to yield an oily yellow residue. The product was crystallized from CHCl$_3$:Et$_2$O at room temperature to yield bright yellow crystals (100 mg, 93%). FTIR (ATR): 3276 cm$^{-1}$ ((O—H stretch), 1601 (C=N stretch), 1053 (C—O stretch). $^1$H NMR (400 MHz, CDCl$_3$): δ (ppm)=7.60 (s, 1H, HC=N), 7.28-7.25 (m, 1H, CH Ar solvent overlap), 7.21-7.15 (m, 3H, 3×CH Ar), 6.68 (s, 1H, CH Ar), 6.61 (d, 1H, $^3$J=8.2 Hz, CH Ar), 4.07 (bs, 2H, CH$_2$), 3.82 (s, 2H, CH$_2$), 3.76-3.70 (m, 6H, 3×CH$_2$), 3.35-3.62 (m, 2H, CH$_2$), 3.53-3.45 (m, 2H, 2×CH$_2$), 2.31 (bs, 1H, OH), 1.37 (d, 6H, $^3$J=6.4 Hz, 2×CH$_3$), 1.14 (d, 6H, $^3$J=6.4 Hz, 2×CH$_3$). $^{13}$C NMR (400 MHz, CDCl$_3$): δ (ppm) =174.90, 159.68, 158.05, 144.63, 141.94, 138.83, 129.41, 127.61, 123.26, 119.22, 111.97 (HC=N and 11 C Ar), 72.67, 70.97, 70.54, 69.62, 67.55, 61.94 (6×CH$_2$), 28.32, 24.60, 23.16 ($^i$Pr). ESI-MS: 518.1536 m/z [M−2Cl]$^{+2}$ (calc. 518.0533 m/z). EA: C$_{50}$H$_{68}$Cl$_2$N$_2$OPd$_2$. Found (calc.): C: 54.77 (54.16), H: 6.04 (6.18), N: 2.40 (2.53).

Synthesis of [(PdCl{4-{2-[2-(2-hydroxyethoxy)ethoxy]ethoxy})}CH=N{2,6-$^i$Pr$_2$-C$_6$H$_3$})$_2$(μ-Ph$_2$P(CH$_2$)$_2$PPh$_2$)] (BTC6)

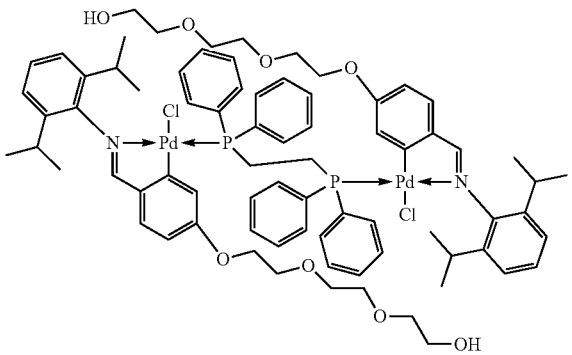

BTC6

B6 (100 mg, 0.107 mmol) was added to DCM (10 mL) at 25° C. The bridge was not fully soluble, so the dppe (43 mg, 0.107 mmol) was added to the solution.

With the addition of the phosphine, the bridge dissolved fully to form a clear yellow solution. After δ hours the reaction mixture was still a clear yellow solution. The solvent was removed to yield a pale-yellow precipitate. The residue was dissolved in a small amount of DCM and layered with Et$_2$O at room temperature. Fine off-white spine-like crystals were filtered off and dried under high vacuum at 50° C. Mp: 110.8-111° C. melt, 152° C. decomposed to black. FTIR (ATR): 3390 cm$^{-1}$ (O—H stretch), 1609 cm$^{-1}$ (C=N stretch), 1098 cm$^{-1}$ (C—O stretch), 1059 cm$^{-1}$ (C—O stretch). $^1$H NMR (600 MHz, CDCl$_3$): δ (ppm)=7.91-7.87 (m, 5H, HC=N and 4×CH Ar dppe), 7.32-7.30 (m, 2H, 2×CH Ar), 7.28-7.24 (m, 6H, 6×CH Ar dppe), 7.19 (d, 2H, $^3$J=7.7 Hz, 2×CH Ar), 6.49 (dd, 1H, $^3$J=8.2 Hz, 4J=2.3 Hz, CH Ar), 5.86-5.85 (m, 1H, CH Ar), 3.68-3.66 (m, 2H, CH$_2$ tether), 3.59-3.57 (m, 2H, CH$_2$ tether), 3.56-3.54 (m, 2H, CH$_2$ tether), 3.49-3.48 (m, 2H, CH$_2$ tether), 3.42 (hept., 2H, $^3$J=6.9 Hz, 2×CH), 3.37-3.36 (m, 2H, CH$_2$ tether), 3.13-3.11 (m, 2H, CH$_2$ tether), 3.02 (s, 2H, CH$_2$ dppe), 2.38 (t, 1H, $^3$J=5.9 Hz, OH), 1.34 (d, 6H, $^3J$=6.8 Hz, 2×CH$_3$), 1.19 (d, 6H, $^3J$=6.9 Hz, 2×CH$_3$). $^{13}$C NMR (151 MHz, CDCl$_3$): δ (ppm)=175.77, 162.59, 160.08, 145.30, 141.47, 140.50, 134.56 (t, $J_{C-P}$), 130.89, 130.61 (t, $J_{C-P}$), 130.16, 128.36 (t, $J_{C-P}$), 126.92, 122.94, 122.56 (t, $J_{C-P}$), 112.50, 72.58 (CH$_2$), 70.75 (CH$_2$), 70.42 (CH$_2$), 69.23 (CH$_2$), 66.85 (CH$_2$), 61.87 (CH$_2$), 29.85, 28.66, 25.55 (t, $J_{C-P}$), 24.59, 23.31. $^{31}$P NMR (243 MHz, CDCl$_3$): δ (ppm)=40.81 (dppe). ESI-MS: found: 630.1804 m/z [M−2Cl]$^{+2}$ (calc. 630.065 m/z), 828.2463 m/z [M−2Cl−L−Pd]$^+$ (calc. 828.2369 m/z). EA: C$_{76}$H$_{92}$Cl$_2$N$_2$O$_8$P$_2$Pd$_2$. Found (calc.): C: 60.16 (60.56), H: 6.20 (6.15), N: 1.82 (1.86).

Turbidimetric Assay—Solubility

The solubility of the compounds was tested according to a standard turbidimetric assay using a 10% DMSO:phosphate buffered saline (PBS) solution.

A 0.01 M pH 7.4 Phosphate Buffered Saline (PBS) solution was prepared by dissolving one PBS tablet (Sigma-Aldrich) in 200 mL distilled water at 25° C. to yield a buffered solution containing 0.01 M phosphate buffer, 0.003 M KCl and 0.14 M NaCl. The solution equilibrated at 25° C. for one hour upon which the pH was confirmed. The buffer was filtered through a 0.45 μM Nylon syringe filter to remove any undissolved particulates.

A 2 mM stock solution in DMSO of each test compound was prepared and filtered through a 0.45 μM PVDF syringe filter prior to use. A preparation plate (96-well flat bottomed) was prepared by serially diluting the compound to achieve the desired concentrations (5.0 μM to 200 μM). The test plate was prepared by pipetting 196 μL DMSO into wells 1-6 and 196 μL PBS into wells 7-12. Each compound was tested in triplicate thus a single plate could be used to evaluate two compounds. 20 μL of each compound concentration was pipetted from the preparation plate into the test plate to bring the total volume up to 200 μL and to ensure that a 10% (v/v) DMSO/PBS solution is achieved. Test plates were prepared in duplicate and one plate was incubated at room temperature (25° C.) and the second at physiological temperature (37° C.). Both test plates were incubated for 2 hours upon which the UV-Vis absorbance readings were measured at 620 nm. The corrected absorbance readings were obtained by subtracting the blank readings from each concentration absorbance.

The turbidimetric assay results are shown in Table 2 below. It is clear from these results that the phosphine bridge as well as the tether plays a role in the aqueous solubility of the palladacycles. In both series, tethered and untethered, the palladacycles with the dppe-bridges were the most soluble (AJ5 and BTC2) when only the influence of the bridge is considered.

With the addition of the tether there is a marked increase in aqueous solubility of the compounds, with the effect particularly pronounced for the dppe bridged compounds BTC2, BTC5 and BTC6. This trend was also observed for the other compounds except for the dppf-bridged compounds (BC4 and BTC4) where the tethered complex was highly insoluble. Based on the results obtained for this tether system, it can be expected that the modified tether systems, for example those of compounds 4 and 6 to 11 in Table 1, would show improved solubility compared to the untethered compounds.

TABLE 2

The results from the turbidimetric assay of the complexes in 10% DMSO:PBS buffer

| Complex | Solubility in 10% DMSO:PBS at 37° C. (μg/mL) |
|---|---|
| AJ5 | 5.98-11.97 |
| BC1 | 10.21-20.41 |
| BC3 | 6.12-12.25 |
| BC4 | 13.65-27.30 |
| BTC1 | 7.06-14.05 |
| BTC2 | 28.38-56.77 |
| BTC3 | 7.12-14.33 |
| BTC4 | n.d. |
| BTC5 | 13.3-26.6 |
| BTC6 | 30.1-60.3 | n.d. = solubility of the complex in 100% DMSO was insufficient to complete the assay.

In Vitro Results

Figures 3, 4:
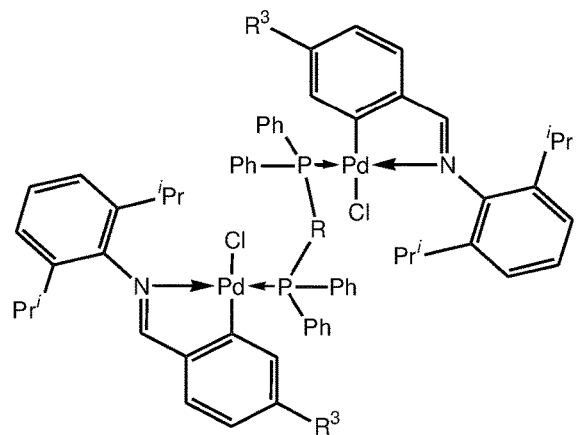
FIG. 3 shows binuclear palladacycles evaluated as potential anti-cancer agents.
FIG. 4 shows a Western Blot analysis indicating γ-H2AX for BTC2, wherein UT=untreated.

In vitro tests were performed to determine if the prepared complexes were active as anti-cancer agents against human breast adenocarcinoma MCF-7 (estrogen receptor positive) and MDA-MB-231 (estrogen receptor negative) cell lines. These included cell viability tests using a MTT assay, and in some cases Western blots to test for DNA damage using γ-H$_2$AX and PARP cleavage to determine whether or not apoptosis takes place. The complexes which were evaluated are shown in FIG. 3.

Cytotoxicity (MTT) Assay

The complex solutions were prepared by dissolution in DMSO to obtain 5 mM stock solutions. Solutions were stored at room temperature for no more than a week. Human MCF-7 breast adenocarcinoma cells in RPMI 1640 medium and human breast adenocarcinoma MDA-MB-231 cells in DMEM were seeded in 96-well plates at 3-6×10$^{-3}$ cells per well. After 48 hours, the cells were treated with various concentrations of complex (0-1 μM) or the vehicle for 48 hours. The 3-(4,5-dimethylthiazol-2-yl)-2,5-diphenyltetrazolium bromide (MTT) assay was then used, as described by the manufacturer's instructions: 10 μL of MTT solution was added to each well. Well plates were then incubated at 37° C. for 4 h. This was followed by addition of 100 μL solubilisation buffer (10% SDS in 0.01 M HCl) and incubation overnight at 37° C. Absorbance at 585 nm was then determined for each well and the mean cell viability was calculated as a percentage of the mean vehicle control. The experiments were performed in triplicate and the data were used to determine the half maximal inhibitory concentration values (IC$_{50}$).

The IC$_{50}$ values are summarised in Table 3 below together with the solubility data. The obtained values were compared to the IC$_{50}$ values of AJ5, the binuclear μ-bisphosphine palladacycle, in the respective cell lines, as the aim was to improve the solubility of the compound, whilst maintaining the same level of activity.

TABLE 3

IC$_{50}$ values and solubilities of various palladacycles

| Complex | IC$_{50}$ (μM) MCF-7 | IC$_{50}$ (μM) MDA-MB-231 | Solubility in 10% DMSO:PBS at 37° C. (μg/mL) |
|---|---|---|---|
| AJ5 | 0.18 ± 0.048 | 0.19 ± 0.015 | 5.98-11.97 |
| BC1 | 2.7 ± 0.21 | 2.2 ± 0.19 | 10.21-20.41 |
| BC3 | 5.8 ± 0.28 | 5.0 ± 0.075 | 6.12-12.25 |
| BC4 | Inactive | Inactive | 13.65-27.30 |
| BTC1 | 2.1 ± 0.21 | 2.5 ± 0.13 | 7.06-14.05 |
| BTC2 | 0.49 ± 0.02 | 0.58 ± 0.012 | 28.38-56.77 |
| BTC3 | 2.5 ± 0.26 | 2.3 ± 0.19 | 7.12-14.33 |

TABLE 3-continued

IC$_{50}$ values and solubilities of various palladacycles

| Complex | IC$_{50}$ (μM) MCF-7 | IC$_{50}$ (μM) MDA-MB-231 | Solubility in 10% DMSO:PBS at 37° C. (μg/mL) |
|---|---|---|---|
| BTC4 | Inactive | Inactive | n.d. |
| BTC5 | 0.41 | 0.5 | 13.3-26.6 |
| BTC6 | 0.36 ± 0.01 | 0.41 ± 0.02 | 30.1-60.3 | n.d. = solubility of the complex in 100% DMSO was insufficient to complete the assay The binuclear complexes do not appear to exhibit any significant selectivity between the two cell lines, as can be seen in from the data in Table 3. The results indicate that dppe may be the optimal bisphosphine ligand for these

| Complex | IC$_{50}$ (μM) MCF-7 | IC$_{50}$ (μM) MDA-MB-231 | Solubility in 10% DMSO:PBS at 37° C. (μg/mL) |
|---|---|---|---|
| AJ5 | 0.18 ± 0.048 | 0.19 ± 0.015 | 5.98-11.97 |
| BC1 | 2.7 ± 0.21 | 2.2 ± 0.19 | 10.21-20.41 |
| BC3 | 5.8 ± 0.28 | 5.0 ± 0.075 | 6.12-12.25 |
| BC4 | Inactive | Inactive | 13.65-27.30 |
| BTC1 | 2.1 ± 0.21 | 2.5 ± 0.13 | 7.06-14.05 |
| BTC2 | 0.49 ± 0.02 | 0.58 ± 0.012 | 28.38-56.77 |
| BTC3 | 2.5 ± 0.26 | 2.3 ± 0.19 | 7.12-14.33 |
| BTC4 | Inactive | Inactive | n.d. |
| BTC5 | 0.41 | 0.5 | 13.3-26.6 |
| BTC6 | 0.36 ± 0.01 | 0.41 ± 0.02 | 30.1-60.3 | compounds, as both AJ5 and its tethered analogue BTC2, as well as the tethered compounds BTC5 and BTC6, appear to be the most active compounds. However, as stated, although the untethered compounds were shown to be active against these cell lines the major problem, including for AJ5, is the poor solubility thereof in aqueous media thereby rendering them clinically unsuitable.

The dppm and dppp compounds which differ from dppe by only one methylene group, showed higher IC$_{50}$ values while the dppf analogues were found to be inactive. The inactivity of the dppf compounds can be explained in terms of their solubility in the test medium, as both BC4 and BTC4 are highly soluble in DMSO (>50 mg/mL) and polar organic solvents, but they are completely intolerant of water, instantly precipitating upon addition of aqueous medium.

Western Blot Assays

After the IC$_{50}$ values were determined Western blot assays were used to determine how the active palladacycle complexes bring about the growth inhibition, as determined by the MTT assay.

The complex solutions were prepared by dissolution in DMSO to obtain 0.1 and 0.2 μM stock solutions. Solutions were stored at room temperature for no more than a week. Human MCF7 breast adenocarcinoma cells in RPMI 1640 medium were plated in 6 cm petri dishes at 6×105 cells per plate. The cells were treated with the complex solutions for 24 or 48 hours. Cells were then lysed using whole cell lysis buffer (0.5 M tris-HCl, pH 6.8, 2% SDS, 10% glycerol, 1% β-mercaptoethanol and 0.02% bromophenol blue). Samples were boiled for 10 minutes. The proteins were resolved using SDS/PAGE (8-15% gels) as required. They were then transferred to Hybond ECL membranes which were then incubated with primary antibodies against PARP ½ (sc-7150), phospho-H2AX (#2577) and p38 (M000). Thereafter, the membranes were incubated with HRP-conjugated secondary antibodies (1:5000). The antibody-reactive proteins were visualised with a chemiluminescence reaction (ECL) detection system.

The most important proteins which are employed as markers for potential anti-cancer drugs are γ-H2AX, which, if present, is an indication of DNA damage and PARP, which if cleaved, is an indication that apoptosis has been induced. In order to allow for relative quantification of the proteins being detected, a loading control, P38, was used to ensure that loading discrepancies are not interpreted as drug-induced changes.

FIG. 4 shows that there is little to no γ-H2AX for the untreated cells. This is expected, as γ-H2AX is a DNA damage response agent which gathers at the site of DNA double-strand breaks. Treatment of the cells with BTC2 for 24 and 48 hours, respectively, show a significant amount of γ-H2AX.

FIG. 5, shows the presence of PARP for both the untreated and treated cells at 0 and 24 hours and little to no cleaved PARP. Drug-induced apoptosis leads to increased amounts of cleaved PARP, the molecular marker of apoptosis. The presence of cleaved PARP (86 KD) in the cells after treatment with BTC2 for 24 hours indicates that BTC2 induces apoptosis. The induction of apoptosis is preferable to necrosis, an alternative form of cell death. Necrosis is a detrimental mode of cell death, leading to inflammation in the host and often it is fatal. Apoptosis or programmed cell death is favourable, as it does not cause undesired negative effects and is usually beneficial to the host. Thus, making the mode of cell death caused by these palladacycles suited to their application as potential anti-cancer agents.

In Vivo Results

Anti-Tumour Activity

The activity of BTC2 was evaluated in two breast cancer cell lines (MCF 7 and MDA-MB-231). The latter is an aggressive, metastatic cell line in which metastasis is often difficult to prevent or control.

The in-vivo activity results show that BTC2 was capable of arresting tumour growth at a rate comparable to that of the positive control drug (paclitaxel). At a concentration of 24.5 μM BTC2 showed 21% tumour regression in the MCF 7 cell line, while paclitaxel showed 26% tumour regression but at a concentration of 50 μM respectively.

In the MDA-MB-231 cell-line, BTC2 was able to induce tumour reduction although not to the same extent as seen for MCF 7. Again, BTC2 was used at about half the concentration of the control, paclitaxel. Therefore, it can be surmised that BTC2 is significantly more active.

Metastasis Reduction

The ability of BTC2 to prevent metastasis was also evaluated.

Metastasis is the process of the spreading of the cancer from its site of origin to other parts of the body. This was evaluated using the same chick embryo model as mentioned above, and again compared to the known drug, paclitaxel.

When tested in the aggressive breast cancer cell line, MDA-MB 231, BTC2 was able to induce a 46% reduction in metastasis compared to 64% reduction for paclitaxel. However, as in the above test, the paclitaxel concentration employed in this experiment was significantly higher than that of BTC2 (50 μM vs 24.4 μM. respectively). It is thus envisaged that at comparable concentrations, BTC2 would further reduce metastasis.

Toxicity

The toxicity of BTC2 was also evaluated.

The number of chick embryos that survived after treatment with the metallodrug was used as an indication of the toxicity. BTC2 when tested in the MCF-7 cell line, showed toxicity behaviour comparable to that of paclitaxel. Between 75 and 80% of the chick embryos survived after 9 days of treatment with BTC2. A similar survival rate was observed even at high concentrations of 50 times the $IC_{50}$ concentration of the drug. Similar behaviour was observed when using the MDA-MB-231 cell line. The low toxicity of BTC2 compares favourably with the clinically approved drug, paclitaxel.

The invention claimed is:

1. A compound of the Formula (I)

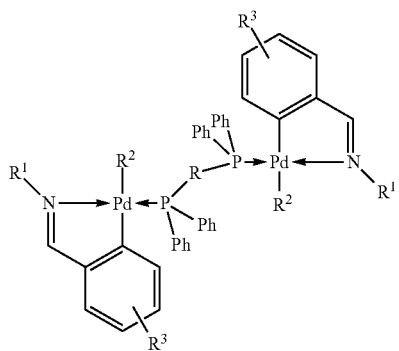

Formula (I)

or a pharmaceutically acceptable salt, stereoisomer, hydrate, or solvate thereof wherein, $R^1$ is phenyl optionally substituted with one or more substituents independently selected from linear or branched $C_{1-4}$ alkyl, hydroxyl, and —$SO_3H$, $R^2$ is independently selected from halogen, —NCS, —SCN, $N_3$, and —$OOCCH_3$, and —$OS(CH_3)_2$, R is $(CH_2)_y$, wherein y is 1-3, $R^3$ is independently one or more substituents selected from hydrogen, and —$O(CH_2CH_2O)_xR^4$, provided that at least one $R^3$ is not hydrogen, wherein x is 1-3, $R^4$ is independently selected from hydrogen, —$CH_2CH_2OH$, and —$CH_2CH_2R^5$, a folic acid group, a monosaccharide group, a disaccharide group, and a fatty acid group, $R^5$ is $C_{1-4}$ alkoxy.

2. The compound according to claim 1, wherein $R^1$ is phenyl optionally substituted with one or more substituents selected from $C_{1-4}$ alkyl.

3. The compound according to claim 1, wherein $R^1$ is phenyl substituted with two occurrences of isopropyl.

4. The compound according to claim 1, wherein $R^2$ is selected from Cl, Br, I, and F.

5. The compound according to claim 4, wherein $R^2$ is Cl.

6. The compound according to claim 1, wherein $R^3$ is independently one or more substituents selected from —$O(CH_2)_2O(CH_2)_2OH$, —$O(CH_2)_2O(CH_2)_2O(CH_2)_2OH$, —$O(CH_2)_2OH$, and —$O(CH_2)_2O(CH_2)_2OCH_3$.

7. The compound according to claim 1, wherein $R^3$ is independently one or more —$O(CH_2)_2OR^4$, wherein $R^4$ is independently selected from a folic acid group, a monosaccharide group, a disaccharide group, and a fatty acid group.

8. The compound of claim 1, wherein the compound is:

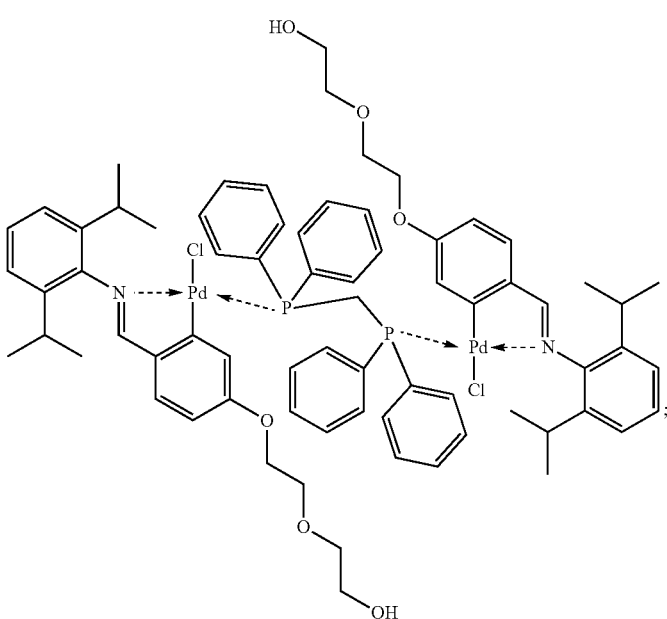

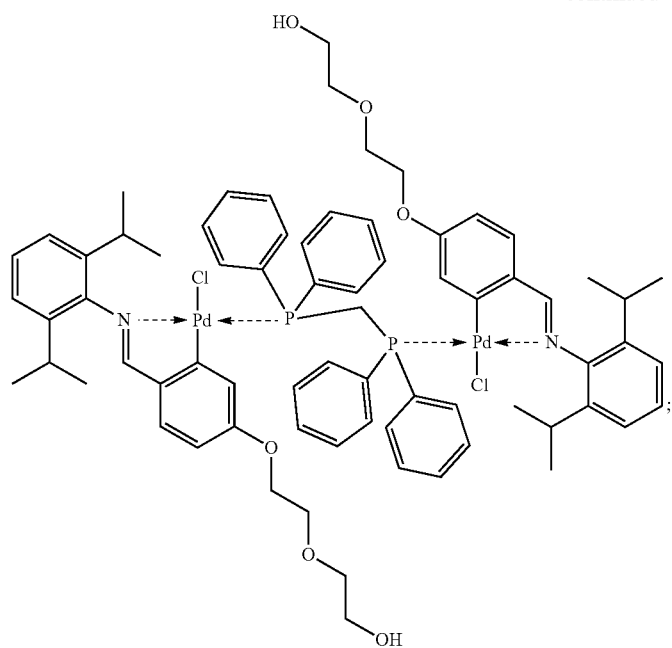
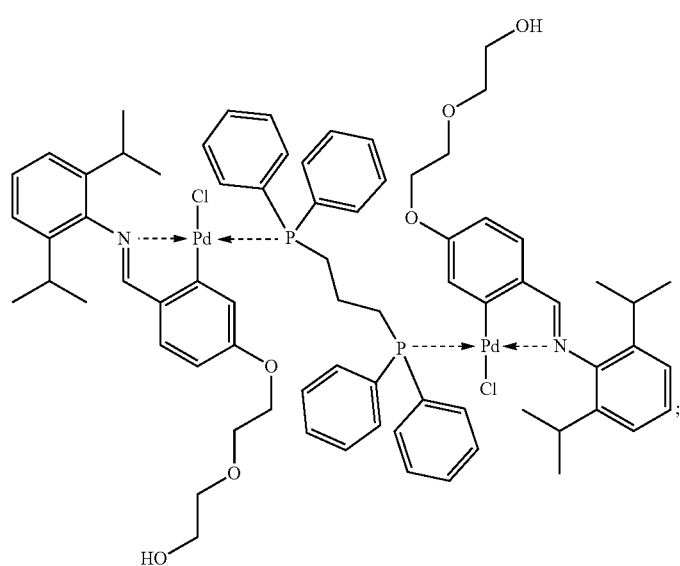

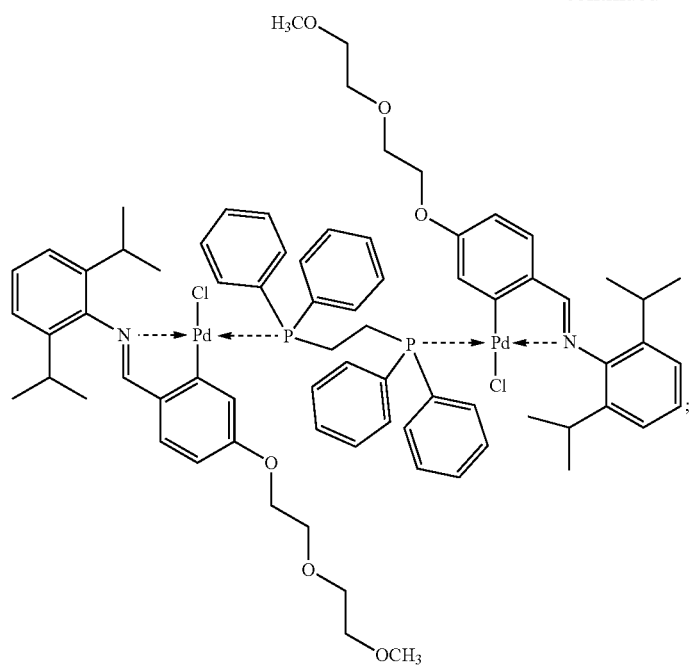
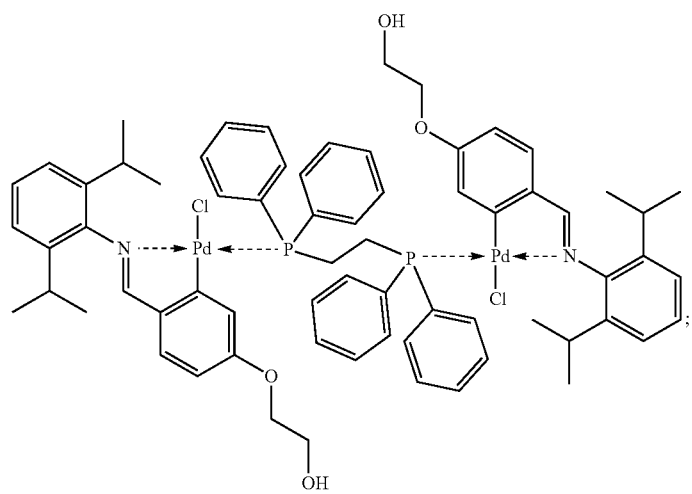

-continued
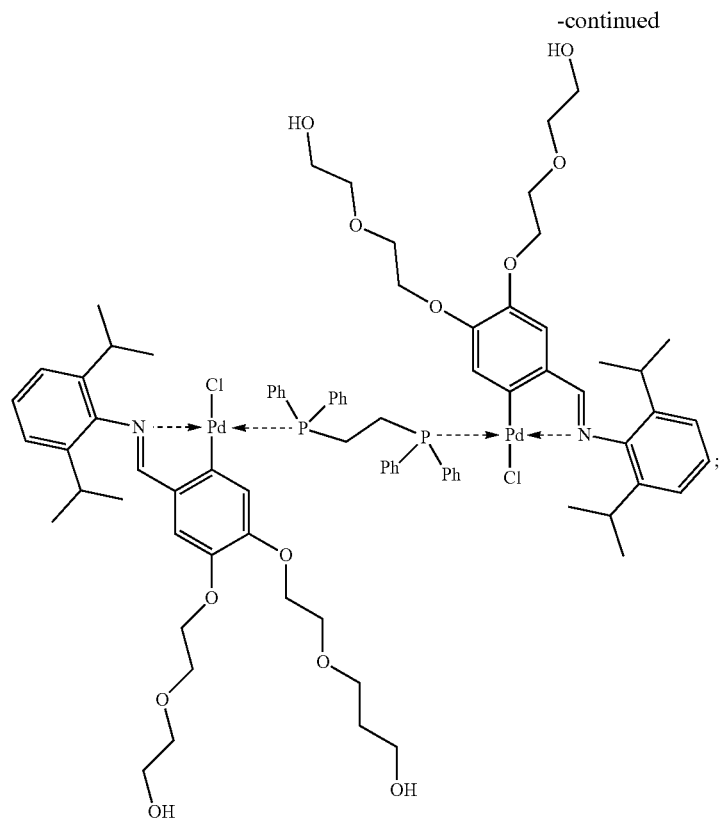
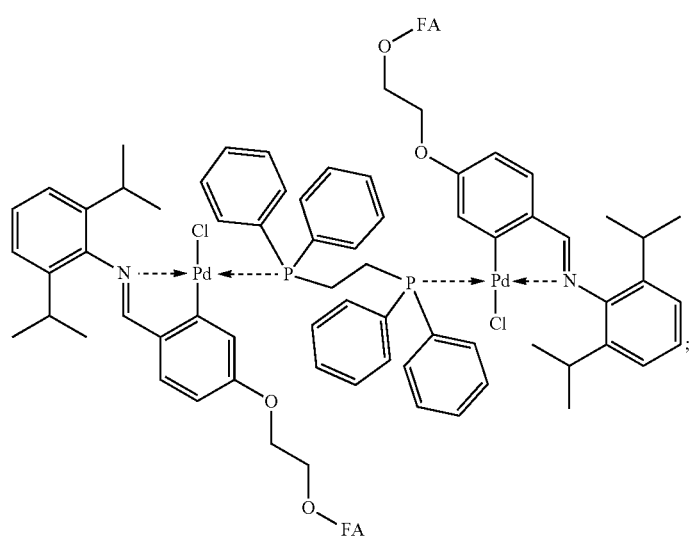

-continued
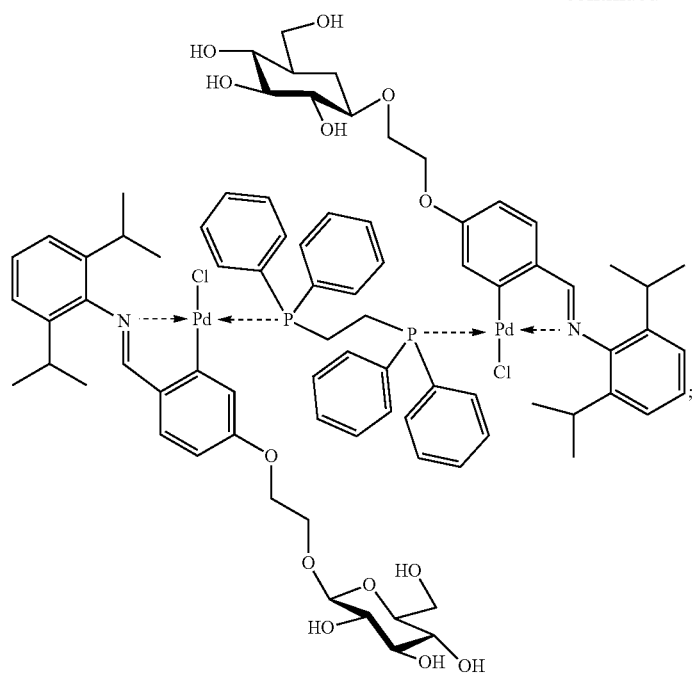
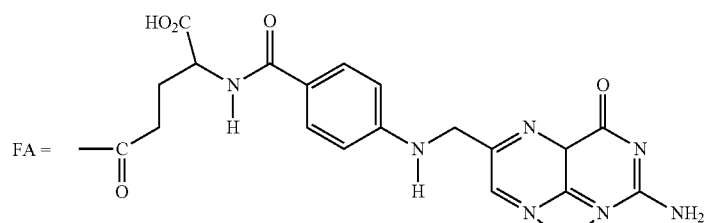
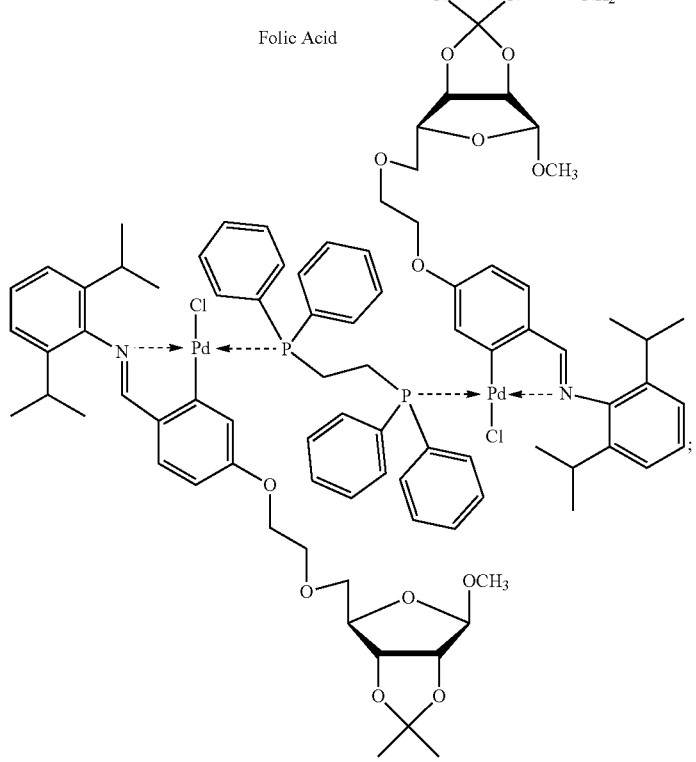

-continued
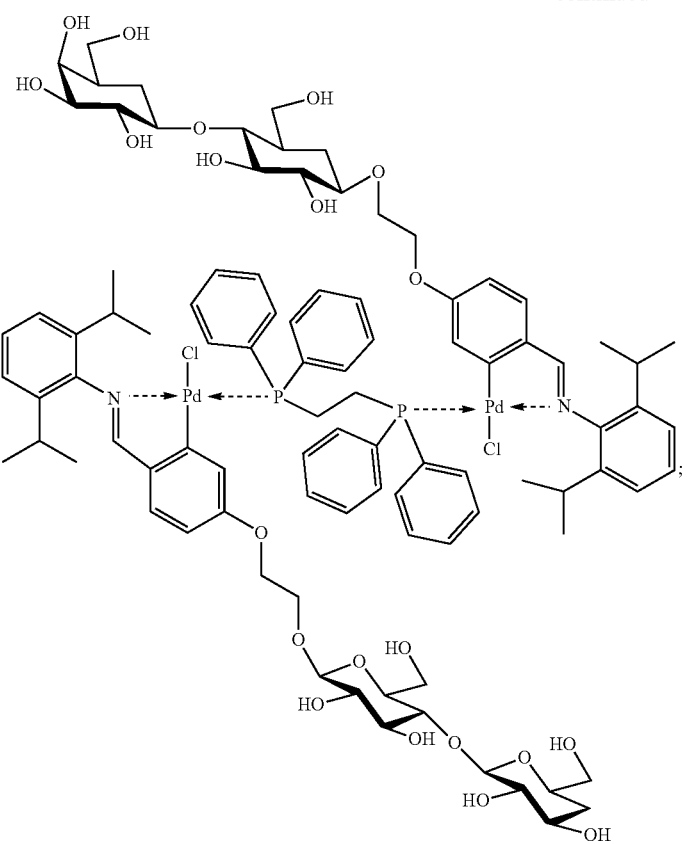
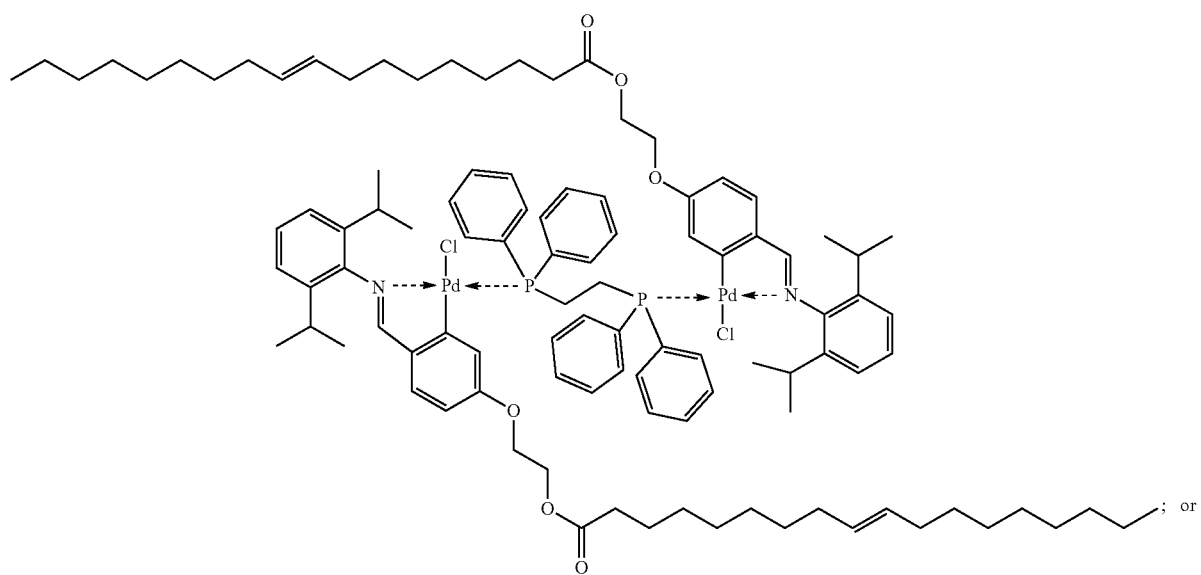

-continued

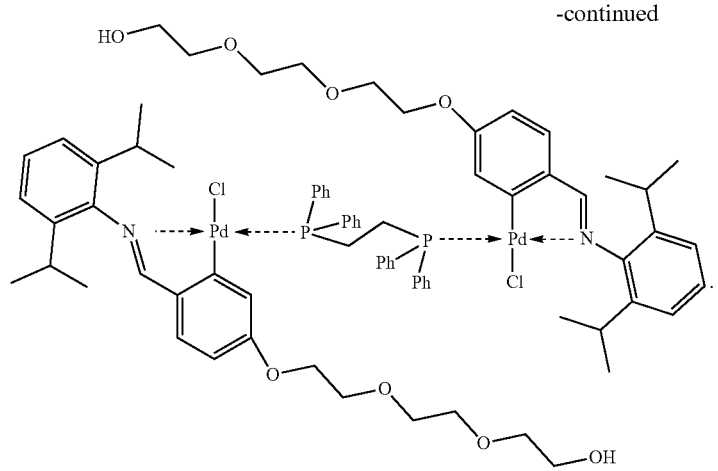

9. A pharmaceutical composition comprising a pharmaceutically acceptable carrier and a pharmaceutically effective amount of a compound according to claim 1.

10. A pharmaceutical composition according to claim 9, wherein the composition comprises a further therapeutic agent.

11. A compound according to claim 1, for use as a medicament.

12. A compound according to claim 1, for use in a method of treating a disease, the method comprising administering a pharmaceutically effective amount of the compound or composition to a subject in need thereof.

13. The compound for use according to claim 12, wherein the disease is cancer.

14. The compound for use according to claim 13, wherein the cancer is selected from breast cancer and skin cancer.

15. A method of treating a disease, the method comprising administering a compound according to claim 1, to a subject in need thereof.

16. The method according to claim 15, wherein the disease is cancer.

17. The method according to claim 16, wherein the cancer is selected from breast cancer and skin cancer.

* * * * *